US007964734B2

(12) United States Patent
Karup et al.

(10) Patent No.: US 7,964,734 B2
(45) Date of Patent: Jun. 21, 2011

(54) RALOXIFENE ACID ADDITION SALTS AND/OR SOLVATES THEREOF, IMPROVED METHOD FOR PURIFICATION OF SAID RALOXIFENE ACID ADDITION SALTS AND/OR SOLVATES THEREOF AND PHARMACEUTICAL COMPOSITIONS COMPRISING THESE

(75) Inventors: Gunnar Leo Karup, Copenhagen S (DK); Søren Bols Pedersen, Hvidovre (DK)

(73) Assignee: A/S Gea Farmaceutisk Fabrik, Hvidovre (DK)

( * ) Notice: Subject to any disclaimer, the term of this patent is extended or adjusted under 35 U.S.C. 154(b) by 1022 days.

(21) Appl. No.: 10/528,691

(22) PCT Filed: Sep. 30, 2003

(86) PCT No.: PCT/DK03/00645
§ 371 (c)(1),
(2), (4) Date: Sep. 21, 2005

(87) PCT Pub. No.: WO2004/029046
PCT Pub. Date: Apr. 8, 2004

(65) Prior Publication Data
US 2006/0154966 A1     Jul. 13, 2006

(30) Foreign Application Priority Data

Sep. 30, 2002  (DK) ................................. 2002 01450

(51) Int. Cl.
*C07D 409/12* (2006.01)
*A61K 31/445* (2006.01)

(52) U.S. Cl. ........................................ 546/212; 514/324
(58) Field of Classification Search .................. 514/324; 546/212
See application file for complete search history.

(56) References Cited

U.S. PATENT DOCUMENTS

| 4,133,814 A | 1/1979 | Jones et al. |
| 4,418,068 A | 11/1983 | Jones |
| 5,852,193 A | 12/1998 | Chelius |

FOREIGN PATENT DOCUMENTS

| EP | 0 062 503 A1 | 10/1982 |
| EP | 0 062 504 A1 | 10/1982 |
| EP | 0 062 505 A1 | 10/1982 |
| EP | 0 584 952 A1 | 3/1994 |
| EP | 0 652 002 A1 | 5/1995 |
| EP | 0 670 162 A1 | 9/1995 |
| EP | 0 674 903 A1 | 10/1995 |
| EP | 0 675 121 A1 | 10/1995 |
| EP | 0 693 488 A1 | 1/1996 |
| EP | 0 699 672 A1 | 3/1996 |
| EP | 0 699 673 A1 | 3/1996 |
| EP | 0 781 555 A1 | 7/1997 |
| EP | 0 826 682 A1 | 3/1998 |
| EP | 0 875 511 A1 | 11/1998 |
| GB | 2 293 382 A | 3/1996 |
| GB | 2 293 602 A | 4/1996 |
| WO | WO 95/34536 | 12/1995 |
| WO | WO 9609045 A1 | 3/1996 |
| WO | WO 96/40676 | 12/1996 |
| WO | WO 96/40677 | 12/1996 |
| WO | WO 96/40678 | 12/1996 |
| WO | WO 96/40691 | 12/1996 |
| WO | WO 96/40693 | 12/1996 |
| WO | WO 97/30709 | 8/1997 |
| WO | WO 97/34888 | 9/1997 |
| WO | WO 97/35571 | 10/1997 |
| WO | WO 98/13369 | 4/1998 |
| WO | WO 98/08513 | 5/1998 |
| WO | WO 98/22456 | 5/1998 |
| WO | WO 98/48787 | 11/1998 |
| WO | WO 98/48792 | 11/1998 |
| WO | WO 98/48793 | 11/1998 |
| WO | WO 98/49156 | 11/1998 |
| WO | WO 00/04880 | 2/2000 |
| WO | WO 00/35485 A1 | 6/2000 |
| WO | WO 0035485 | 6/2000 |
| WO | WO 00/50007 | 8/2000 |
| WO | WO 01/23369 A2 | 4/2001 |
| WO | WO 02/42261 A2 | 5/2002 |
| WO | WO 02/42289 A2 | 5/2002 |
| WO | WO 2004/029046 A2 | 4/2004 |
| WO | WO 2005/003116 A1 | 1/2005 |

OTHER PUBLICATIONS

Seddon "Pseudopolymorph . . . " Crystal Growth and design p. 1087 (2004) (internet print out).*
Braga et al. "Making crystals from . . . " Chem. Commun. p. 3635-3645 92005).*
Seddon "Pseudopolymorph . . . " Cryst. growth and design 4(6) 1087 (2004) two page from internet.*

(Continued)

*Primary Examiner* — Celia Chang
(74) *Attorney, Agent, or Firm* — Sughrue Mion, PLLC

(57) ABSTRACT

Raloxifene acid addition salts or solvates thereof, having improved dissolution properties in media comprising hydrochloric acid are described, compared with similar preparations based on raloxifene or raloxifene hydrochloride. The disclosed acid addition salts or solvates thereof show an improved bioavailability in media comprising hydrochloric acid, such as the gastric juice. The acid addition salts or solvates thereof are addition salts or solvates of raloxifene and a pharmaceutical acceptable acid selected among succinic acid, lactic acid, malonic acid or sulphuric acid. Further, crystalline forms of the raloxifene salts and solvates thereof are disclosed. The raloxifene acid addition salts and/or solvates thereof are useful for the preparation of pharmaceutical composition for oral administration capable of fast and reliable release of the active ingredients in the stomach of the patient, in particular for the treatment of cancer or osteoporosis, or for inhibiting cartilage degradation. A new method for preparation of raloxifene lactate is also disclosed.

4 Claims, 12 Drawing Sheets

OTHER PUBLICATIONS

Muzaffar et al. "Polymorphism and drug availability" J. Phar. 1(1) 59-66 (1979).*
Jain et al. "Polymorphisom in pharmacey" Indian Drugs 23(g)315-329 (1986).*
Doelker et al. "Crystalline modification . . . " CA 138:209993 (2002).*
Doelker et al. "Physicochemical behavior or active . . . " CA 132:325872 (2000).*
Otsuka et al. "Effect of polymorphic . . . " Chem. Pharm. bull 47(6)852-856 (1999).*
Lanz "Pharmaceutical powder tecnology . . . " Basal (2006) p. 1-4.*
CMU Pharmaceutical polymorphism, internet print out (2008) p. 1-3.*
Yokoda et al. "Chiral separation . . . "J. Chem. Eng. Japan v.37(10) p. 1284-1285 (2004).*
Fasel et al. "Amplification of chirality . . . " Nature v.439, January, p. 449-452 (2006).*
Zhang et cl. "Racemic species of . . . " J. pharm. Sci. v.92(7) p. 1356-1366 (2003).*
Exhibit I, search result for C34H33NO7S/MF (2010).*
Antiestrogens. 2.[1]. Structure-Activitiy Studies. in a Series of 3-Aroyl-2-arylbenzo [b] thien-3-yl[4-[2-(1-piperidinyl) ethosy]-phenyl]methanone Hydrochloride (LY156758), a Remarkably Effective Estrogen Antagonist with Only Minimal Intrinsic Estrogenicity, by C.D. Jones, et al. J. Med. Chem., vol. 27(8), 1057-1066.

* cited by examiner

RALOXIFENE ACID ADDITION SALTS AND/OR SOLVATES THEREOF, IMPROVED METHOD FOR PURIFICATION OF SAID RALOXIFENE ACID ADDITION SALTS AND/OR SOLVATES THEREOF AND PHARMACEUTICAL COMPOSITIONS COMPRISING THESE

The invention relates to acid addition salts and/or solvates of [6-hydroxy-2-(4-hydroxyphenyl)benzol[1)]thien-3-yl][4-[2-(1-piperidinyl)-ethoxy]phenyl-, raloxifene, having high availability from media comprising dilute hydrochloric acid, such as gastric juice. In addition useful crystal forms of the acid addition salts and/or solvates are disclosed.

In another aspect the invention relates to pharmaceutical composition for oral administration comprising said novel acid addition salts and/or solvates thereof, preferably in crystalline form. The pharmaceutical compositions according to the invention are useful because the high availability from dilute hydrochloric acid, such as gastric juice, secures a high and reliable release of the active ingredient, raloxifene, in the stomach of the patient to whom said pharmaceutical composition have been administered.

Further the invention provides an improved method for preparation and purification of said acid addition salts and/or solvates thereof, which method provides for a quick and highly efficient purification of the crude raloxifene product.

BACKGROUND FOR THE INVENTION

Raloxifene, [6-hydroxy-2-(4-hydroxyphenyl)benzol[b]thien-3-yl][4-[2-(1-piperidinyl)ethoxy]phenyl-, is a well known compound having antiestrogen and antiandrogen activity. Raloxifene or raloxifene hydrochloride has proved useful for the preparation of pharmaceutical compositions for the treatment of cancer, osteoporosis and cartilage degradation.

Raloxifene, [6-hydroxy-2-(4-hydroxyphenyl)benzol[b]thien-3-yl][4-[2-(1-piperidinyl)ethoxy]phenyl-, is also known as 6-hydroxy-2-(4-hydrophenyl)-3-[4-(2-piperidinoethoxy)-benzoyl]benzo-[b]-thiophene. Other names for raloxifene may also be found in the literature.

EP 62 503 A1 discloses benzothiophene compounds and process for preparing them. The disclosed compounds have antiestrogenic and antiandrogenic activity. Pharmaceutical preparation comprising said benzothiophene compounds are described, which preparations are useful for the treatment of cancers. A particular preferred compound is Raloxifene. Acid addition salts of the benzothiophene compounds with physiologically acceptable acids are also disclosed. As examples of physiologically acceptable acids are mentioned among others sulphuric acid, succinic acid and lactic acid.

In the manufacture of raloxifene the crude product in the reaction mixture was evaporated to dryness, redissolved and purified in several steps before the pure product was recovered as a crude product that was further purified to provide the desired compound.

The obtained free base was subsequent transformed into acid addition salts using usual techniques.

EP 584 952 discloses use of raloxifene or acid addition salts thereof for the treatment of osteoporosis. It is preferred to use an acid addition salt of raloxifene instead of raloxifene as a free base because the acid addition salts generally have improved dissolution properties compared to the free base. As examples of acids used for the acid addition salts are mentioned among others: hydrochloric acid, sulphuric acid, lactic acid, malonic acid and succinic acid. Raloxifene hydrochloride is the preferred acid addition salt.

EP 652 002 A1 discloses use or 2-phenyl-3-aroylbenzothiephenes or pharmaceutical acceptable acid addition salts thereof, such as raloxifene and raloxifene hydrochloride respectively, for the inhibition of cartilage degradation.

In WO 96/09045 raloxifene hydrochloride in crystalline form or as a solvate is described.

EP 910 369 discloses raloxifene hydrochloride in crystal form where the crystals are smaller than 50 microns, and EP 826 682 discloses raloxifene in an amorphous form having enhanced solubility.

At present most commercial available pharmaceutical compositions comprising raloxifene as active ingredient comprises raloxifene hydrochloride, because raloxifene hydrochloride is fairly soluble in aqueous solvents whereas raloxifene as free base is only sparingly soluble in aqueous solvents.

Despite the extensive experimentation of increasing the bioavailability of raloxifene there is still a need for providing the active compound in a form having increased availability of the active compound in order to provide pharmaceutical preparations for oral administration, which composition have a high availability of the active compound raloxifene from the upper gastrointestinal tract.

BRIEF DESCRIPTION OF THE INVENTION

The present invention relates to raloxifene acid addition salts and/or solvates having a high availability in dilute hydrochloric acid or gastric juice.

The present inventors have surprisingly discovered that the raloxifene acid addition salts and solvates according to the invention have high bioavailability of the active compound soon after ingestion. In particular the raloxifene salts and/or solvates according to the invention have improved intrinsic dissolution properties in the presence of hydrochloric acid such as in gastric juice, compared with the commonly used raloxifene acid addition salt, raloxifene hydrochloride.

In a further aspect the invention relates to new and particular useful crystal forms of said novel raloxifene acid addition salts or solvates thereof.

In an even further aspect the invention relates to pharmaceutical compositions comprising said novel raloxifene acid addition salts and solvates thereof, which compositions after the ingestion thereof is capable of releasing the active compound raloxifene in higher amounts, compared with the frequently used compound raloxifene hydrochloride.

A further aspect of the invention relates to a new and improved method for preparation of raloxifene lactate.

SHORT DESCRIPTION OF THE FIGURES

DETAILED DESCRIPTION OF THE INVENTION

Figure 1:
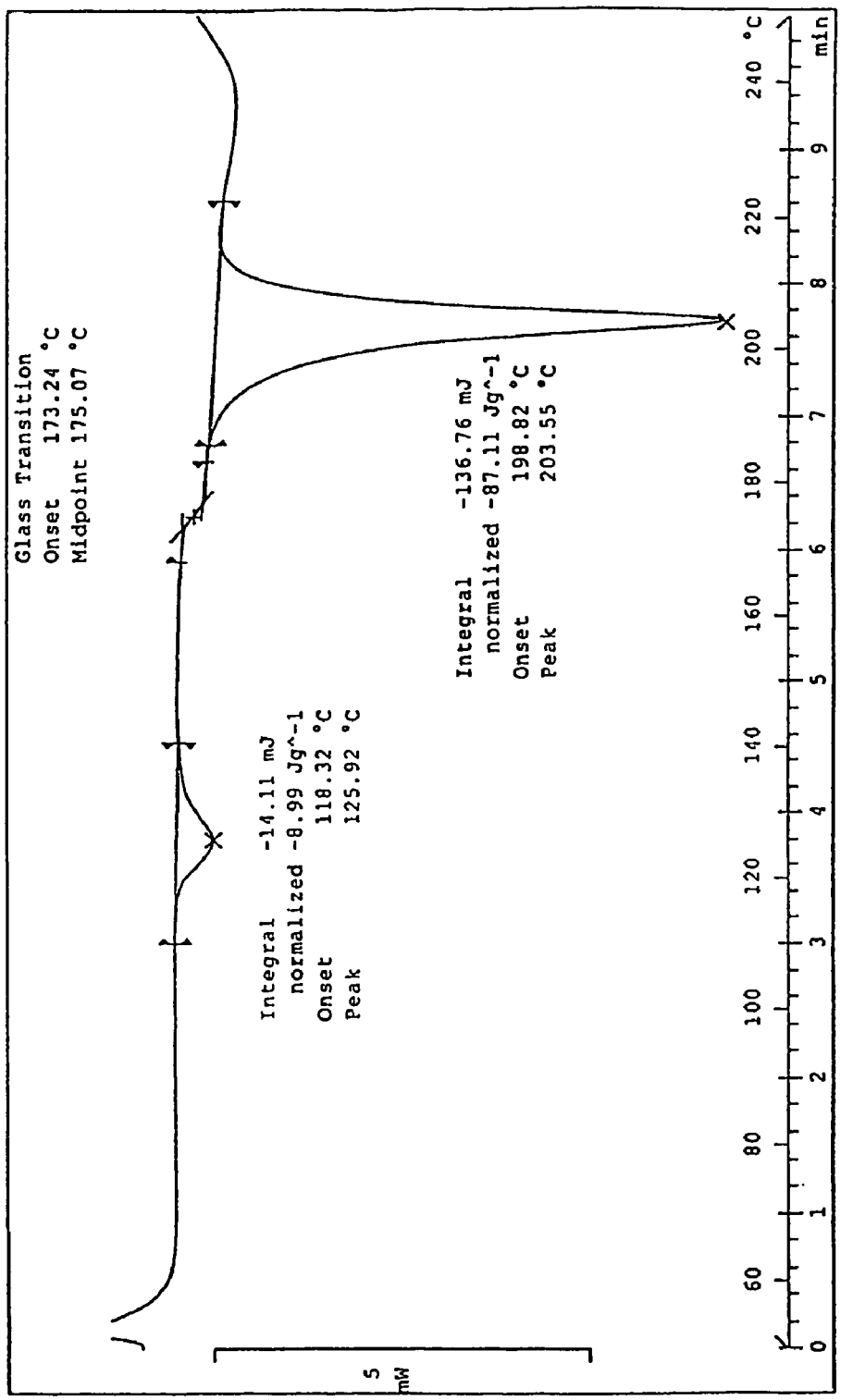
FIG. 1 shows a differential scanning calorimetric chart (DSC) for raloxifene DL-lactate. The chart was recorded at a rate of 20° C./min.

The inventors have realized that even though raloxifene hydrochloride is fairly soluble in aqueous media the solubility appear to decreases significant in aqueous media comprising hydrochloric acid.

By the term "dilute hydrochloric acid" or "media comprising hydrochloric acid" as used herein is meant an acidic aqueous solution containing chloride ions. Gastric juice is a preferred example of dilute hydrochloric acid.

The skilled person will appreciate that gastric juice contains hydrochloric acid. Further the skilled person will appreciate that the composition of gastric juice apart from individual variations depends on various factors such as time of day, time since last meal and size and composition of said last meal. However for the purpose of the present description, the gastric juice can be regarded as a dilute solution of hydrochloric acid usually having a pH value in the range of approximately 1-3, possible also containing sodium chloride in an amount of 1-3% w/w. In the duodenum and the upper part of the small intestines the pH raises up to approximately 4-6 or even higher.

The raloxifene acid addition salts and/or solvates thereof according to the invention have dissolution properties in dilute hydrochloric that secure a high bioavailability of these compounds. In particular the compounds according to the invention have higher intrinsic dissolution rates in dilute hydrochloric acid compared with free raloxifene or raloxifene hydrochloride.

The terms "high availability", "high bioavailability" or grammatical equivalent expressions are according to the invention intended to mean that the raloxifene salts and/or solvates thereof are available for assimilation from the gastro intestinal tract to the circulation of the body in high amount soon after ingestion. In particular the raloxifene salts and/or solvates thereof have higher bioavailability compared with the presently frequently used raloxifene compounds, i.e. raloxifene as free base or raloxifene hydrochloride.

In accordance with the present invention the term "upper gastrointestinal tract" is intended to mean the oesophagus, the stomach, the duodenum and the upper part of the small intestines. It is believed that the assimilation of raloxifene mainly takes place in the upper gastrointestinal tract.

The inventors have surprisingly discovered that acid addition salts and/or solvates thereof according to the invention appear to have a higher bioavailability from acidic solutions comprising sodium chloride compared to raloxifene as free base or raloxifene hydrochloride in crystalline or amorphous form. Consequently, pharmaceutical preparations for oral administration comprising acid addition salts and/or solvates thereof according to the invention will provide the active compound raloxifene faster and/or in an higher amount compared with pharmaceutical preparations comprising raloxifene hydrochloride or raloxifene as free base.

Thus in one aspect the invention provides pharmaceutical preparations for oral administration comprising a raloxifene acid addition salt and/or solvate thereof according to the invention as the active ingredient. These preparations provide the active compound raloxifene in a form having high bioavailability when said preparations are ingested and dispersed in gastric juice.

The high availability of the active compound secures that a therapeutic regimen using the pharmaceutical preparations according to the invention may be performed with higher accuracy because the attending physician will know that the complete dose or at least a major part thereof will be available for assimilation from the gastro intestinal tract soon after the ingestion the pharmaceutical preparations according to the invention.

Therefore pharmaceutical compositions comprising such compounds may provide for a higher efficiency of the of said compounds by the individuals to whom said compositions are administered, compared with corresponding pharmaceutical compositions based on raloxifene or raloxifene hydrochloride.

Thus the pharmaceutical preparations according to the invention provide a fast and high availability of the active compound in the stomach soon after intake of the preparation.

Alternatively or additionally, the high availability of the active compounds according to the invention may render the need for micronization superfluous, which micronization in the prior art have been used to increase the bioavailability of raloxifene compounds, cf. EP 910 369.

Therefore in one aspect the present invention relates to pharmaceutical compositions for oral administration comprising raloxifene acid addition salts and/or solvates thereof, having fast and high bioavailability of the active compound raloxifene.

According to the invention the acid addition salts and/or solvates of raloxifene is selected among the succinate, lactate, malonate or the sulphate.

The lactate may be in the D or L form or a mixture thereof such as racemic mixtures. Further the lactate may be isolated as a solvate.

Because succinic acid, malonic acid and sulphuric acid have two acid groups per molecule, compounds of these acids and raloxifene may be isolated as either mono or di acid addition salts and/or solvates thereof having either one or two raloxifene molecules per acid molecule respectively.

In a preferred embodiment the acid addition salt and/or solvates thereof according to the invention is raloxifene DL-lactate, and in a particular preferred embodiment the acid addition salt is raloxifene L-lactate.

The skilled person will appreciate that the acid addition salts according to the invention may be isolated as solvates, which in the present description is to be understood as compounds where solvate molecules are included in the solid compounds, usually in defined stoichiometric amounts.

For some compounds more that one solvate may be isolated, which solvates differ only with respect of the solvent incorporated in the solid and the number of solvate molecules per molecule of the acid addition salt.

Preferred solvates according to the invention are solvates with pharmaceutically acceptable solvents such as water or alcohols having less than 5 carbon atoms, even more preferred selected among water, methanol, ethanol, propanol and 2-propanol.

Examples of solvates according to the invention include raloxifene L-lactate hemihydrate, raloxifene D-lactate hemihydrate, raloxifene DL-lactate hemihydrate, raloxifene L-lactate ¼-hydrate, raloxifene D-lactate ¼-hydrate, raloxifene DL-lactate ¼-hydrate and raloxifene sulphate (2-propanol solvate).

Preferred compounds according to the invention include raloxifene D-lactate hemihydrate, raloxifene DL-lactate hemihydrate, raloxifene L-lactate hemihydrate and raloxifene L-lactate ¼-hydrate, where raloxifene L-lactate hemihydrate and raloxifene L-lactate ¼-hydrate is particular preferred.

It is well known that organic compounds may be isolated in crystalline form or in amorphous form. Generally it is preferred to provide compounds in crystalline form because crystallisation usually is accompanied by a purification of the compound, and further, because crystals are more well defined solids than amorphous materials the properties of compounds in crystalline form varies less than materials in amorphous form.

Therefore the raloxifene acid addition salts and/or solvates according to the invention in crystalline form provides another aspect of the invention.

The raloxifene acid addition salts in crystalline form according to the invention are raloxifene lactate, raloxifene malonate and raloxifene succinate, which all exist as distinct crystalline compounds, and raloxifene sulphate, which may be isolated in crystalline form as a 2-propanol solvate having one molecule of 2-propanol incorporated per two raloxifene molecules.

For some of the raloxifene acid addition salts and/or solvates thereof according to the invention more that one crystal form may be possible, where the different crystal forms may be prepared dependent on the solvent, temperature etc, as it will be known within the area.

Pharmaceutical preparations for oral administration comprising raloxifene salts and/or solvates thereof according to the invention may be prepared using pharmaceutical techniques well known within the area e.g. from text books such as Remington's manual.

For example may the raloxifene compounds according to the invention be formed for oral administration into tablets, capsules etc. In forming the pharmaceutical preparations the compounds according to the invention may be mixed with usual fillers and excipients, such as disintegration agents, lubricants, swelling agents. The preparations may also be coated according to well-known techniques.

Raloxifene acid addition salts and/or solvates may be prepared using methods known for the skilled person.

For example may any acid addition salt be converted into the free base and subsequently the free base may be converted into another acid addition salt by known procedures.

Usually raloxifene is prepared directly as raloxifene hydrochloride.

The present inventors have observed that in contrast to raloxifene and previously tested acid addition salts thereof e.g. raloxifene hydrochloride, raloxifene lactate can easily be crystallized in high yield and high purity from an alcoholic solution.

It has been realized that this property may be used for a quick and high efficient purification of raloxifene lactate from an intermediate in the synthesis of raloxifene.

Thus raloxifene lactate may be prepared directly without previous isolation of free raloxifene or raloxifene hydrochloride using the following procedure:

To a solution of the compound having the general formula I

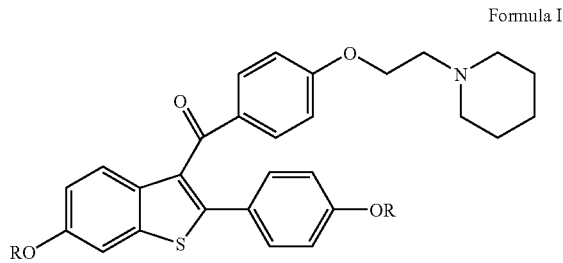

Formula I wherein R represents two independently selected hydroxyl protection groups, in a solvent a suitable reagent is added in order to remove the protection groups. Next the pH of the mixture is adjusted to neutral reaction using lactic acid, and thereafter raloxifene lactate may be precipitated and isolated.

This procedure according to the invention is beneficial because raloxifene lactate is easily crystallized from such a mixture, particular if the solvent is an alcohol having 1-5 carbon atoms. The easy crystallisation of raloxifene lactate represents a high and easy purification of the raloxifene from the reaction mixture. The crystallized raloxifene lactate may be further purified by recrystallization from an alcohol.

The compound having the formula I is known within the art from e.g EP 875 511 A1, where it is called formula VII, and from EP 62 503, where it is prepared by the reaction scheme (B).

The group R may be any hydroxyl protection group known to the skilled person. For example, R may be selected from $C_1$-$C_4$ alkyl, $C_5$-$C_7$ cycloalkyl, benzyl —$COR^2$ or $SO_2R^2$, wherein $R^2$ is $C_1$-$C_4$ primary or secondary alkyl, $C_1$-$C_3$ fluoroalkyl, $C_1$-$C_3$ chloroalkyl, $C_1$-$C_4$ alkylphenyl, $C_1$-$C_4$ alkoxyphenyl, mono- or dinitrophenyl or mono- or di(chloro or fluoro)phenyl.

The two R groups may be the same or different. It is preferred that the two R groups are selected so that the similar conditions are needed to remove the two groups.

The term "neutral reaction" is intended to mean that the mixture has a pH value in the range of 6-8, preferably 7.0-7.5.

The chemical used to remove the protection groups may be any chemical known to be able to remove the particular used protection groups. It is within the skills of the practitioner to select a suitable chemical to remove the protection group for each selected protection group.

The solvent used for the reaction may in principle be any solvent that is capable of dissolving the reagents and does not participate in reactions with any of the ingredients of the reaction mixture under the conditions applied. Preferred solvents are alcohols having 1 to 5 carbon atoms. Particular preferred solvents are monovalent alcohols having 1 to 5 carbon atoms, where methanol, ethanol, propanol and 2-propanol are the most preferred solvents.

The obtained raloxifene lactate may be recrystallized in order to obtain the compound in even higher purity.

As solvent for the crystallization may in principle be used any alcohol having suitable melting and boiling temperatures. Alcohols having 1 to 5 carbon atoms and one hydroxyl group are preferred.

As examples of preferred alcohols can be mentioned methanol, ethanol, propanol, 2-propanol, butanol, 2-butanol, neobutyl alcohol, pentanol, 2-pentanol and 3-pentanol.

It is within the abilities of the skilled practitioner to select a suitable solvent for crystallization of particular selected compound of the invention.

Ethanol is a particular preferred alcohol.

The concentration of alcohol in the crystallization mixture should be higher that 90%, preferably higher that 95%. A particular preferred solvent for the crystallisation reaction is 96% ethanol.

The crystallisation may be performed using procedures known within the area. Further as it will be known for the skilled person it may be advantageous to add seeding crystals to the crystallization mixture to promote crystallisation.

Thus in another aspect the invention relates to a method for purification of raloxifene lactate from an alcoholic solution of raloxifene comprising addition of lactate, adjusting pH and temperature of the obtained mixture and isolation of the formed crystalline raloxifene lactate.

In a preferred embodiment the alcoholic solution of raloxifene is the reaction mixture of the synthesis of raloxifene if necessary after a change of solvent.

The invention is further illustrated by way of examples, which are solely provided for illustration and should not be considered at limiting in any way.

EXAMPLES

Example 1

[6-hydroxy-2-(4-hydroxyphenyl)benzo[b]thien-3-yl] [4-[2-(1-piperidinyl)ethoxy]phenyl-, succinate; Raloxifene succinate 37.9 g (~0.6 mol) pulverized potassium hydroxide (>85%) is dissolved in 1250 ml 2-propanol, with stirring and addition of nitrogen, over approximately 30 minutes. 100 g (0.196 mol) raloxifene hydrochloride is added in small portions in such a way that temperature is kept below 30° C. After addition of raloxifene hydrochloride, the deep red suspension is stirred for 30-45 minutes until a deep red solution appears. Reminiscence of insoluble product may be filtered off. 1 L of a solution of 70.85 g (0.6 mol) succinic acid in 2-propanol/water (80:20) is added with violent stirring during 1-1.5 hours. The mixture is now stirred further at room temperature for 18 hours, and the precipitate is filtered off as white/yellowish crystals. The product is now washed 2 times with 40 ml 2-propanol and then dried in vacuo at 55-65° C. for 16 hours to give 178.5 g crude product.

The crude product is stirred with 890 ml of water for 3 hours and then filtered off and washed 3 times with 100 ml of water. The product is dried in vacuo at 55-65° C. for 16 hours to give 89.7 g (77.3% yield) of product.

Mp: dec. >195° C., mp. ~225° C.

Elemental analysis $C_{33}H_{33}NO_8S$:

Calculated: C, 64.96%; H, 5.62%; N, 2.37%; S, 5.42%.

Found: C, 65.64%; H, 5.49%; N, 2.60%; S, 5.99%.

IR:

3406 cm$^{-1}$, 3145 cm$^{-1}$, 2945 cm$^{-1}$, 2691 cm$^{-1}$, 1642 cm$^{-1}$, 1597 cm$^{-1}$, 1541 cm$^{-1}$, 1501 cm$^{-1}$, 1457 cm$^{-1}$, 1430 cm$^{-1}$, 1421 cm$^{-1}$, 1356 cm$^{-1}$, 1259 cm$^{-1}$, 1234 cm$^{-1}$, 1171 cm$^{-1}$, 1125 cm$^{-1}$, 1108 cm$^{-1}$, 1079 cm$^{-1}$, 1047 cm$^{-1}$, 1038 cm$^{-1}$, 907 cm$^{-1}$, 839 cm$^{-1}$, 807 cm$^{-1}$, 623 cm$^{-1}$

XRD:

| D | 2Theta | I(rel) | I(abs) | FWHM |
|---|---|---|---|---|
| 13.195230 | 6.6933 | 20.78 | 8475 | 0.1400 |
| 9.695642 | 9.1137 | 13.43 | 5476 | 0.0300 |
| 9.304945 | 9.4972 | 18.19 | 7419 | 0.1300 |
| 8.394523 | 10.5300 | 13.26 | 5407 | 0.1000 |
| 7.944460 | 11.1283 | 14.15 | 5768 | 0.1000 |
| 7.708667 | 11.4699 | 17.61 | 7180 | 0.1200 |
| 7.526675 | 11.7482 | 12.32 | 5023 | 0.0898 |
| 7.323294 | 12.0756 | 15.22 | 6205 | 0.1000 |
| 7.160495 | 12.3512 | 13.04 | 5316 | 0.0800 |
| 6.926815 | 12.7696 | 23.68 | 9655 | 0.1300 |
| 6.606409 | 13.3917 | 29.08 | 11856 | 0.1400 |
| 6.463392 | 13.3894 | 14.45 | 5891 | 0.0898 |
| 6.285432 | 14.0789 | 21.24 | 8662 | 0.1200 |
| 6.127742 | 14.4432 | 63.63 | 25947 | 0.1200 |
| 5.961999 | 14.8469 | 15.55 | 6342 | 0.0900 |
| 5.875574 | 15.0665 | 15.77 | 6430 | 0.0898 |
| 5.788967 | 15.2933 | 16.15 | 6585 | 0.1400 |
| 5.624221 | 15.7441 | 34.74 | 14167 | 0.1200 |
| 5.453763 | 16.2394 | 22.89 | 9334 | 0.1300 |
| 5.276560 | 16.7887 | 12.71 | 5182 | 0.1200 |
| 5.095057 | 17.3913 | 14.19 | 5786 | 0.1100 |
| 5.020392 | 17.6520 | 11.12 | 4535 | 0.0898 |
| 4.835944 | 18.3309 | 18.30 | 7461 | 0.1200 |
| 4.765096 | 18.6059 | 18.62 | 7591 | 0.1100 |
| 4.630456 | 19.1519 | 65.88 | 26864 | 0.1600 |
| 4.525518 | 19.6003 | 15.16 | 6180 | 0.0800 |
| 4.484997 | 19.7792 | 24.48 | 9982 | 0.1000 |
| 4.376528 | 20.2745 | 18.78 | 7659 | 0.1000 |
| 4.352225 | 20.3889 | 19.11 | 7790 | 0.1000 |
| 4.227757 | 20.9959 | 29.39 | 11984 | 0.1000 |
| 4.191265 | 21.1808 | 56.82 | 23171 | 0.0800 |
| 4.158052 | 21.3520 | 40.16 | 16377 | 0.0898 |
| 4.101947 | 21.6475 | 17.14 | 6988 | 0.0800 |
| 4.062068 | 21.8626 | 19.79 | 8072 | 0.1000 |
| 4.010082 | 22.1496 | 11.70 | 4771 | 0.0600 |
| 3.921660 | 22.6556 | 100.00 | 40776 | 0.1300 |
| 3.860487 | 23.0194 | 29.04 | 11842 | 0.1100 |
| 3.813566 | 23.3066 | 19.25 | 7850 | 0.1100 |
| 3.732687 | 23.8189 | 19.33 | 7884 | 0.1300 |
| 3.694791 | 24.0669 | 22.47 | 9161 | 0.1100 |
| 3.644300 | 24.4054 | 18.84 | 7680 | 0.1400 |
| 3.544078 | 25.1067 | 13.63 | 5556 | 0.0700 |
| 3.496160 | 25.4565 | 16.28 | 6637 | 0.0898 |
| 3.446458 | 25.8299 | 20.36 | 8300 | 0.2100 |
| 3.398344 | 26.2021 | 12.35 | 5036 | 0.1200 |
| 3.373032 | 26.4022 | 8.82 | 3597 | 0.0898 |
| 3.305938 | 26.9481 | 14.08 | 5741 | 0.1100 |
| 3.281940 | 27.1489 | 10.08 | 4112 | 0.0898 |
| 3.260437 | 27.3314 | 9.66 | 3937 | 0.0898 |
| 3.227083 | 27.6194 | 19.22 | 7838 | 0.1200 |
| 3.179256 | 28.0434 | 16.28 | 6640 | 0.2600 |
| 3.146269 | 28.3435 | 8.89 | 3627 | 0.0898 |
| 3.121159 | 28.5764 | 9.58 | 3907 | 0.0900 |
| 3.097691 | 28.7975 | 10.64 | 4337 | 0.0400 |
| 3.074307 | 29.0213 | 19.64 | 8008 | 0.1200 |
| 3.032262 | 29.4328 | 10.17 | 4148 | 0.1300 |
| 3.010128 | 29.6541 | 9.43 | 3847 | 0.0898 |

Example 2

[6-hydroxy-2-(4-hydroxyphenyl)benzo[b]thien-3-yl] [4-[2-(1-piperidinyl)ethoxy]phenyl-, malonate; Raloxifene malonate 37.9 g (~0.6 mol) pulverized potassium hydroxide (>85%) is dissolved in 1250 ml 2-propanol, with stirring and addition of nitrogen, over approximately 30 minutes. 100 g (0.196 mol) raloxifene hydrochloride is added in small portions in such a way that temperature is kept below 30° C. After addition of raloxifene hydrochloride, the deep red suspension is stirred for 30-45 minutes until a deep red solution appears. Reminiscence of insoluble product may be filtered off. 260 ml of a solution of 62.76 g (0.6 mol) malonic acid in 2-propanol/water is added with violent stirring during 1-1.5 hours. The mixture is now stirred further at room temperature for 18 hours, and the precipitate is filtered off as white/yellowish crystals. The product is now washed 2 times with 40 ml 2-propanol and then dried in vacuo at 55-65° C. for 16 hours to give 182.4 g crude product.

The crude product is stirred with 912 ml of water for 3 hours and then filtered off and dried in vacuo at 55-65° C. for 16 hours to give 98.7 g (87.2% yield) of crude product. The crude product is boiled for 5 minutes in 500 ml 2-propanol and then cooled at 10° C. for 30 minutes. The product is filtered off and washed with 100 ml 2-propanol and then dried in vacuo to give 90.8 g (97%) of the product.

Mp: 226-227° C.

Elemental analysis $C_{32}H_{31}NO_8S$:

Calculated: C, 64.46%; H, 5.41%; N, 2.42%; S, 5.55%.

Found: C, 64.86%; H, 5.55%; N, 2.57%; S, 5.87%.

IR:

3388 cm$^{-1}$, 3199 cm$^{-1}$, 2950 cm$^{-1}$, 2683 cm$^{-1}$, 2543 cm$^{-1}$, 1643 cm$^{-1}$, 1597 cm$^{-1}$, 1539 cm$^{-1}$, 1502 cm$^{-1}$, 1467 cm$^{-1}$, 1421 cm$^{-1}$, 1355 cm$^{-1}$, 1306 cm$^{-1}$, 1255 cm$^{-1}$, 1169 cm$^{-1}$, 1038 cm$^{-1}$, 952 cm$^{-1}$, 907 cm$^{-1}$, 839 cm$^{-1}$, 808 cm$^{-1}$, 645 cm$^{-1}$, cm$^{-1}$, 623 cm$^{-1}$

XRD:

| D | 2Theta | I(rel) | I(abs) | FWHM |
|---|---|---|---|---|
| 14.385166 | 6.1391 | 36.51 | 6471 | 0.0100 |
| 13.125024 | 6.7292 | 38.91 | 6896 | 0.1300 |
| 10.305386 | 8.5734 | 37.32 | 6614 | 0.1700 |
| 9.279238 | 9.5236 | 39.85 | 7062 | 0.1300 |
| 8.860721 | 9.9745 | 34.60 | 6133 | 0.0900 |
| 8.510328 | 10.3863 | 33.27 | 5895 | 0.0900 |
| 8.314361 | 10.6318 | 33.02 | 5852 | 0.0800 |
| 7.947949 | 11.1234 | 41.61 | 7375 | 0.1600 |
| 7.265135 | 12.1727 | 35.79 | 6343 | 0.1300 |
| 6.882996 | 12.8512 | 29.65 | 5254 | 0.0300 |
| 6.537915 | 13.5326 | 60.19 | 10667 | 0.1800 |
| 6.258251 | 14.1404 | 61.12 | 10833 | 0.2100 |
| 6.003203 | 14.7444 | 31.92 | 5657 | 0.1200 |
| 5.877911 | 15.0605 | 29.17 | 5170 | 0.0600 |
| 5.794580 | 15.2784 | 29.33 | 5198 | 0.0200 |
| 5.663226 | 15.6349 | 49.63 | 8796 | 0.1300 |
| 5.550457 | 15.9547 | 36.61 | 6487 | 0.0800 |
| 5.354103 | 16.5438 | 55.84 | 9897 | 0.2200 |
| 5.134028 | 17.2583 | 30.18 | 5349 | 0.1378 |
| 5.023848 | 17.6397 | 55.21 | 9784 | 0.2100 |
| 4.836637 | 18.3283 | 36.13 | 6404 | 0.1400 |
| 4.700761 | 18.8628 | 71.64 | 12696 | 0.1600 |
| 4.644808 | 19.0922 | 86.46 | 15323 | 0.1500 |
| 4.538522 | 19.5436 | 61.36 | 10874 | 0.1300 |
| 4.472256 | 19.8361 | 50.40 | 8931 | 0.1000 |
| 4.347111 | 20.4132 | 37.86 | 6709 | 0.1000 |
| 4.247918 | 20.8951 | 88.12 | 15616 | 0.2300 |
| 4.161428 | 21.3344 | 73.93 | 13101 | 0.1600 |
| 4.085803 | 21.7341 | 37.19 | 6591 | 0.1100 |
| 4.019584 | 22.0966 | 35.60 | 6309 | 0.1500 |
| 3.921695 | 22.6554 | 100.00 | 17722 | 0.1700 |
| 3.765729 | 23.6059 | 50.70 | 8986 | 0.2000 |
| 3.703455 | 24.0097 | 34.79 | 6166 | 0.1200 |
| 3.638542 | 24.4446 | 47.30 | 8382 | 0.1900 |
| 3.499221 | 25.4339 | 44.29 | 7849 | 0.2000 |
| 3.426872 | 25.9801 | 43.63 | 7732 | 0.2200 |
| 3.292398 | 27.0610 | 23.39 | 4145 | 0.1000 |
| 3.253755 | 27.3886 | 25.03 | 4435 | 0.1400 |
| 3.192249 | 27.9269 | 22.18 | 3931 | 0.1400 |
| 3.094846 | 28.8246 | 28.68 | 5083 | 0.3000 |
| 3.034329 | 29.4123 | 27.30 | 4338 | 0.1900 |

Example 3

[6-hydroxy-2-(4-hydroxyphenyl)benzo[b]thien-3-yl] [4-[2-(1-piperidinyl)ethoxy]phenyl-, sulphate (2-propanol solvate); Raloxifene sulphate (2-propanol solvate)

3.79 g (~0.06 mol) pulverized potassium hydroxide (>85%) is dissolved in 125 ml 2-propanol, with stirring and addition of nitrogen, over approximately 30 minutes. 10 g (0.0196 mol) raloxifene hydrochloride is added in small portions in such a way that temperature is kept below 30° C. After addition of raloxifene hydrochloride, the deep red suspension is stirred for 30-45 minutes until a deep red solution appears. Reminiscence of insoluble product may be filtered off A solution of 6.5 g 96% (0.6 mol) sulphuric acid in 15 ml 2-propanol and 12 ml of water is added with violent stirring during 1-1.5 hours (weakly exothermic). The mixture is now stirred further at room temperature for 18 hours, and the precipitate is filtered off as white crystals. The product is now washed 2 times with 4 ml 2-propanol and then dried in vacuo at 55-65° C. for 16 hours to give 15 g crude product.

The crude product is stirred with 76 ml of water for 3 hours and then filtered off and washed 3 times with 100 ml of water. The product is dried in vacuo at 55-65° C. for 16 hours to give 8.6 g (% yield) of product. The product is boiled with 38 ml of 2-propanol for 5 minutes and then cooled on to 0-5° C. for 30 minutes and filtered. The product is washed with 2 times with 5 ml 2-propanol, and dried in vacuum at 70-75° C.

Mp: 262-263° C.

Elemental analysis $C_{59}H_{64}N_2O_{13}S_3$:

Calculated: C, 64.46%; H, 5.41%; N, 2.42%; S, 5.55%.

Found: C, 64.86%; H, 5.55%; N, 2.57%; S, 5.87%.

IR:

3199 cm$^{-1}$, 2963 cm$^{-1}$, 2723 cm$^{-1}$, 2693 cm$^{-1}$, 2659 cm$^{-1}$, 2559 cm$^{-1}$, 1653 cm$^{-1}$, 1597 cm$^{-1}$, 1547 cm$^{-1}$, 1501 cm$^{-1}$, 1467 cm$^{-1}$, 1437 cm$^{-1}$, 1419 cm$^{-1}$, 1344 cm$^{-1}$, 1308 cm$^{-1}$, 1268 cm$^{-1}$, 1251 cm$^{-1}$, 1233 cm$^{-1}$, 1167 cm$^{-1}$, 1037 cm$^{-1}$, 1020 cm$^{-1}$, 952 cm$^{-1}$, 907 cm$^{-1}$, 839 cm$^{-1}$, 823 cm$^{-1}$, 809 cm$^{-1}$, 627 cm$^{-1}$, 524 cm$^{-1}$.

XRD:

| D | 2Theta | I(rel) | I(abs) | FWHM |
|---|---|---|---|---|
| 14.374007 | 6.1439 | 26.57 | 5009 | 0.0900 |
| 10.303750 | 8.5748 | 29.62 | 5583 | 0.1300 |
| 9.201529 | 9.6042 | 26.22 | 4942 | 0.1100 |
| 8.871726 | 9.9621 | 29.84 | 5624 | 0.1300 |
| 8.569965 | 10.3138 | 22.25 | 4195 | 0.0400 |
| 8.320378 | 10.6241 | 25.97 | 4896 | 0.1200 |
| 7.945119 | 11.1274 | 38.65 | 7286 | 0.1300 |
| 7.514174 | 11.7678 | 20.56 | 3876 | 0.1041 |
| 7.205108 | 12.2745 | 25.04 | 4721 | 0.1400 |
| 6.537437 | 13.5336 | 66.78 | 12590 | 0.1400 |
| 6.228787 | 14.2076 | 21.88 | 4126 | 0.1100 |
| 5.628329 | 15.7325 | 20.71 | 3904 | 0.0900 |
| 5.540447 | 15.9837 | 27.40 | 5166 | 0.1100 |
| 5.322476 | 16.5489 | 64.98 | 12249 | 0.1500 |
| 5.138694 | 17.2425 | 21.65 | 4082 | 0.1100 |
| 5.020317 | 17.6522 | 64.05 | 12074 | 0.1400 |
| 4.706881 | 18.8381 | 100.00 | 18851 | 0.1300 |
| 4.618097 | 19.2036 | 60.47 | 11400 | 0.0800 |
| 4.538129 | 19.5453 | 59.35 | 11189 | 0.1100 |
| 4.471816 | 19.8381 | 67.03 | 12636 | 0.1200 |
| 4.261964 | 20.8255 | 54.78 | 10327 | 0.1100 |
| 4.204757 | 21.1121 | 51.35 | 9680 | 0.1600 |
| 4.156029 | 21.3625 | 46.65 | 8794 | 0.1041 |
| 4.093305 | 21.6938 | 25.93 | 4888 | 0.0900 |
| 4.035960 | 22.0058 | 24.21 | 4563 | 0.1800 |

-continued

| D | 2Theta | I(rel) | I(abs) | FWHM |
|---|--------|--------|--------|------|
| 3.937182 | 22.5651 | 25.37 | 4784 | 0.1200 |
| 3.835400 | 23.1721 | 22.17 | 4179 | 0.0900 |
| 3.796528 | 23.4127 | 40.94 | 7718 | 0.0900 |
| 3.767170 | 23.5978 | 61.03 | 11505 | 0.1100 |
| 3.691303 | 24.0899 | 20.10 | 3790 | 0.1500 |
| 3.639317 | 24.4393 | 47.20 | 8897 | 0.1200 |
| 3.590489 | 24.7769 | 28.23 | 5321 | 0.1600 |
| 3.511060 | 25.3467 | 29.66 | 5592 | 0.1100 |
| 3.478586 | 25.5873 | 23.70 | 4468 | 0.1041 |
| 3.416539 | 26.0601 | 37.38 | 7047 | 0.1900 |
| 3.355389 | 26.5436 | 20.28 | 3823 | 0.1300 |
| 3.314637 | 26.8760 | 17.08 | 3220 | 0.1200 |
| 3.271015 | 27.2413 | 15.24 | 2874 | 0.0600 |
| 3.252583 | 27.3987 | 14.71 | 2773 | 0.1041 |
| 3.100446 | 28.7714 | 23.04 | 4344 | 0.1200 |
| 3.079703 | 28.9694 | 19.73 | 3720 | 0.1041 |
| 3.033828 | 29.4172 | 29.23 | 5511 | 0.1300 |
| 3.009744 | 29.6580 | 15.28 | 2880 | 0.1041 |
| 2.937725 | 30.4024 | 13.30 | 2507 | 0.1700 |

Example 4

[6-hydroxy-2-(4-hydroxyphenyl)benzo[b]thien-3-yl]
[4-[2-(1-piperidinyl)ethoxy]phenyl-, DL-lactate;
Raloxifene DL-lactate 37.9 g (~0.6 mol) pulverized potassium hydroxide (>85%) is dissolved in 1250 ml 2-propanol, with stirring and addition of nitrogen, over approximately 30 minutes. 100 g (0.196 mol) raloxifene hydrochloride is added in small portions in such a way that temperature is kept below 30° C. After addition of raloxifene hydrochloride, the deep red suspension is stirred for 30-45 minutes until a deep red solution appears. Reminiscence of insoluble product may be filtered off. A solution of 67.6 g 85% DL-lactic acid (0.6 mol) in 200 ml of 2-propanol is added with violent stirring during 1-1.5 hours. The mixture is now stirred further at room temperature for 18 hours, and the precipitate is filtered off as white/yellowish crystals. The product is now washed 2 times with 40 ml 2-propanol and then dried in vacuo at 55-65° C. for 16 hours to give 109 g crude product.

The crude product is stirred with 545 ml of water for 3 hours and then filtered off and washed 2 times with 75 ml of water. The product is dried in vacuo at 75-80° C. for 16 hours to give 92.7 g (83.9% yield) of product.

Mp: 196-198° C.

Elemental analysis $C_{34}H_{33}NO_7S$:

Calculated: C, 65.00%; H, 5.98%; N, 2.45%; S, 5.60%.

Found: C, 65.07%; H, 5.93%; N, 2.37%; S, 5.34%.

IR:

3385 cm$^{-1}$, 3223 cm$^{-1}$, 2940 cm$^{-1}$, 2675 cm$^{-1}$, 1641 cm$^{-1}$, 1598 cm$^{-1}$, 1542 cm$^{-1}$, 1502 cm$^{-1}$, 1467 cm$^{-1}$, 1421 cm$^{-1}$, 1349 cm$^{-1}$, 1307 cm$^{-1}$, 1253 cm$^{-1}$, 1171 cm$^{-1}$, 1123 cm$^{-1}$, 1038 cm$^{-1}$, 953 cm$^{-1}$, 908 cm$^{-1}$, 837 cm$^{-1}$, 808 cm$^{-1}$, 649 cm$^{-1}$, 623 cm$^{-1}$, cm$^{-1}$, 532 cm$^{-1}$, 514 cm$^{-1}$.

The product was further analysed using differential scanning calorimetry using a METTLER TOLEDO STAR® system, according to the instructions of the manufacturer. The differential scanning calorimetric chart (DSC) is shown in FIG. 1.

Figure 2:
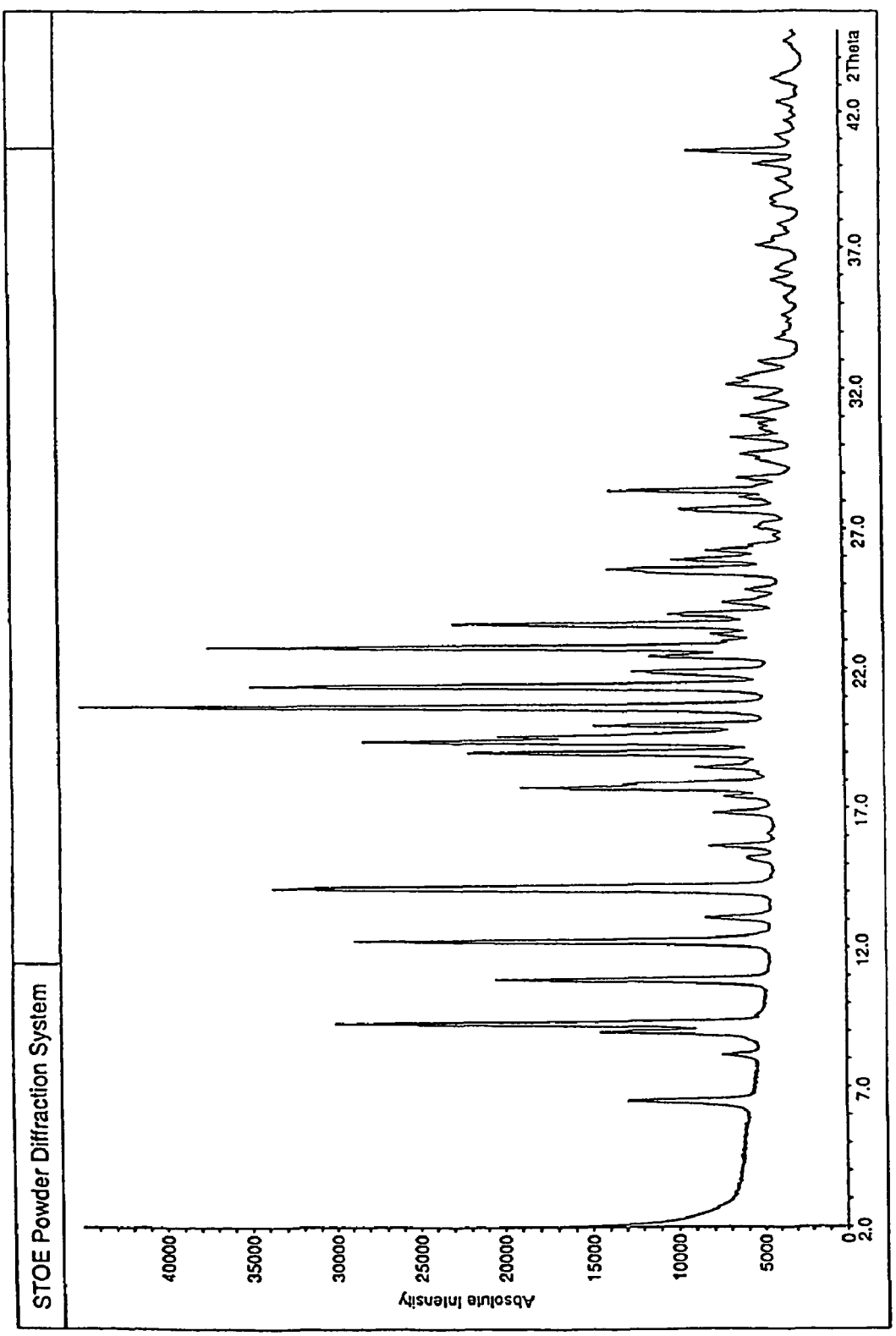
FIG. 2 shows the X-ray diffraction pattern for crystalline raloxifene DL-lactate.

Further the product was analysed by X-ray diffraction analysis using the STOE Powder diffraction system. The result is shown in FIG. 2, and is also listed numerically below.

XRD:

| D | 2Theta | I(rel) | I(abs) | FWHM |
|---|--------|--------|--------|------|
| 13.595814 | 6.4959 | 28.40 | 12683 | 0.1400 |
| 10.855533 | 8.1382 | 16.15 | 7211 | 0.1200 |
| 9.849394 | 8.9711 | 32.17 | 14369 | 0.1000 |
| 9.534325 | 9.2682 | 66.95 | 29898 | 0.1300 |
| 8.150249 | 10.8465 | 45.20 | 20188 | 0.1300 |
| 7.240730 | 12.2138 | 63.53 | 28374 | 0.1400 |
| 6.769843 | 13.0670 | 18.42 | 8227 | 0.1500 |
| 6.272666 | 14.1077 | 75.67 | 33794 | 0.1900 |
| 5.818832 | 15.2143 | 13.28 | 5933 | 0.2000 |
| 5.657337 | 15.6513 | 18.07 | 8070 | 0.1300 |
| 5.505030 | 16.0872 | 10.51 | 4692 | 0.1000 |
| 5.261933 | 16.8357 | 17.48 | 7806 | 0.1400 |
| 5.089504 | 17.4104 | 16.14 | 7210 | 0.1000 |
| 5.001569 | 17.7189 | 41.94 | 18732 | 0.0900 |
| 4.958950 | 17.8725 | 29.16 | 13023 | 0.1148 |
| 4.797388 | 18.4795 | 19.39 | 8660 | 0.1100 |
| 4.669322 | 18.9910 | 49.20 | 21972 | 0.1400 |
| 4.574684 | 19.3876 | 63.21 | 28227 | 0.1000 |
| 4.533019 | 19.5676 | 44.94 | 20071 | 0.1148 |
| 4.440548 | 19.9792 | 32.70 | 14604 | 0.1200 |
| 4.301886 | 20.6301 | 100.00 | 44659 | 0.1500 |
| 4.155406 | 21.3657 | 78.00 | 34833 | 0.1600 |
| 4.059049 | 21.8797 | 27.53 | 12296 | 0.1800 |
| 3.960846 | 22.4285 | 25.59 | 11427 | 0.1000 |
| 3.907408 | 22.7393 | 83.48 | 37282 | 0.1200 |
| 3.865461 | 22.9894 | 16.46 | 7350 | 0.1148 |
| 3.828892 | 23.2120 | 17.46 | 7798 | 0.0900 |
| 3.773130 | 23.5599 | 50.71 | 22649 | 0.1200 |
| 3.716486 | 23.9243 | 23.06 | 10300 | 0.1300 |
| 3.652238 | 24.3515 | 15.79 | 7053 | 0.1800 |
| 3.584725 | 24.8174 | 12.91 | 5764 | 0.1500 |
| 3.486791 | 25.5261 | 30.45 | 13600 | 0.1200 |
| 3.439149 | 25.8858 | 22.21 | 9919 | 0.1300 |
| 3.396267 | 26.2184 | 17.86 | 7978 | 0.1100 |
| 3.370045 | 26.4261 | 12.48 | 5572 | 0.1148 |
| 3.329320 | 26.7553 | 9.21 | 4113 | 0.1100 |
| 3.292728 | 27.0582 | 11.81 | 5274 | 0.1000 |
| 3.278070 | 27.1815 | 11.25 | 5026 | 0.1148 |
| 3.218620 | 27.6935 | 21.24 | 9485 | 0.1900 |
| 3.167986 | 28.1452 | 13.80 | 6162 | 0.0900 |
| 3.143230 | 28.3715 | 30.33 | 13546 | 0.1000 |
| 3.095423 | 28.9191 | 14.02 | 6260 | 0.1200 |
| 3.024921 | 29.5058 | 11.56 | 5161 | 0.1400 |
| 3.007253 | 29.6831 | 13.40 | 5984 | 0.1300 |

Example 5

[6-hydroxy-2-(4-hydroxyphenyl)benzo[b]thien-3-yl]
[4-[2-(1-piperidinyl)ethoxy]phenyl-, L-lactate; Raloxifene L-lactate 37.9 g (~0.6 mol) pulverized potassium hydroxide (>85%) is dissolved in 1250 ml 2-propanol, with stirring and addition of nitrogen, over approximately 30 minutes. 100 g (0.196 mol) raloxifene hydrochloride is added in small portions in such a way that temperature is kept below 30° C. After addition of raloxifene hydrochloride, the deep red suspension is stirred for 30-45 minutes until a deep red solution appears. Reminiscence of insoluble product may be filtered off.

A solution of 67.6 g 85% L-lactic acid (0.6 mol) is added with violent stirring during 1-1.5 hours. The mixture is now stirred further at room temperature for 18 hours, and the precipitate is filtered off as white/yellowish crystals. The product is now washed 2 times with 40 ml 2-propanol and then dried in vacuo at 55-65° C. for 16 hours to give 109 g crude product.

The crude product is stirred with 545 ml of water for 3 hours and then filtered off and washed 2 times with 75 ml of water. The product is dried in vacuo at 75-80° C. for 16 hours to give 92.7 g (83.9% yield) of product.

Mp: 134-136° C.
Elemental analysis $C_{31}H_{33}NO_7S$ (½$H_2O$):
Calculated: C, 65.00%; H, 5.98%; N, 2.45%; S, 5.60%.
Found: C, 65.08%; H, 6.14%; N, 2.58%; S, 5.78%.
IR:
3167 $cm^{-1}$, 2934 $cm^{-1}$, 1641 $cm^{-1}$, 1627 $cm^{-1}$, 1593 $cm^{-1}$, 1543 $cm^{-1}$, 1500 $cm^{-1}$, 1469 $cm^{-1}$, 1433 $cm^{-1}$, 1350 $cm^{-1}$, 1314 $cm^{-1}$, 1259 $cm^{-1}$, 1170 $cm^{-1}$, 1128 $cm^{-1}$, 1103 $cm^{-1}$, 1033 $cm^{-1}$, 908 $cm^{-1}$, 836 $cm^{-1}$, 809 $cm^{-1}$.

Figure 3:
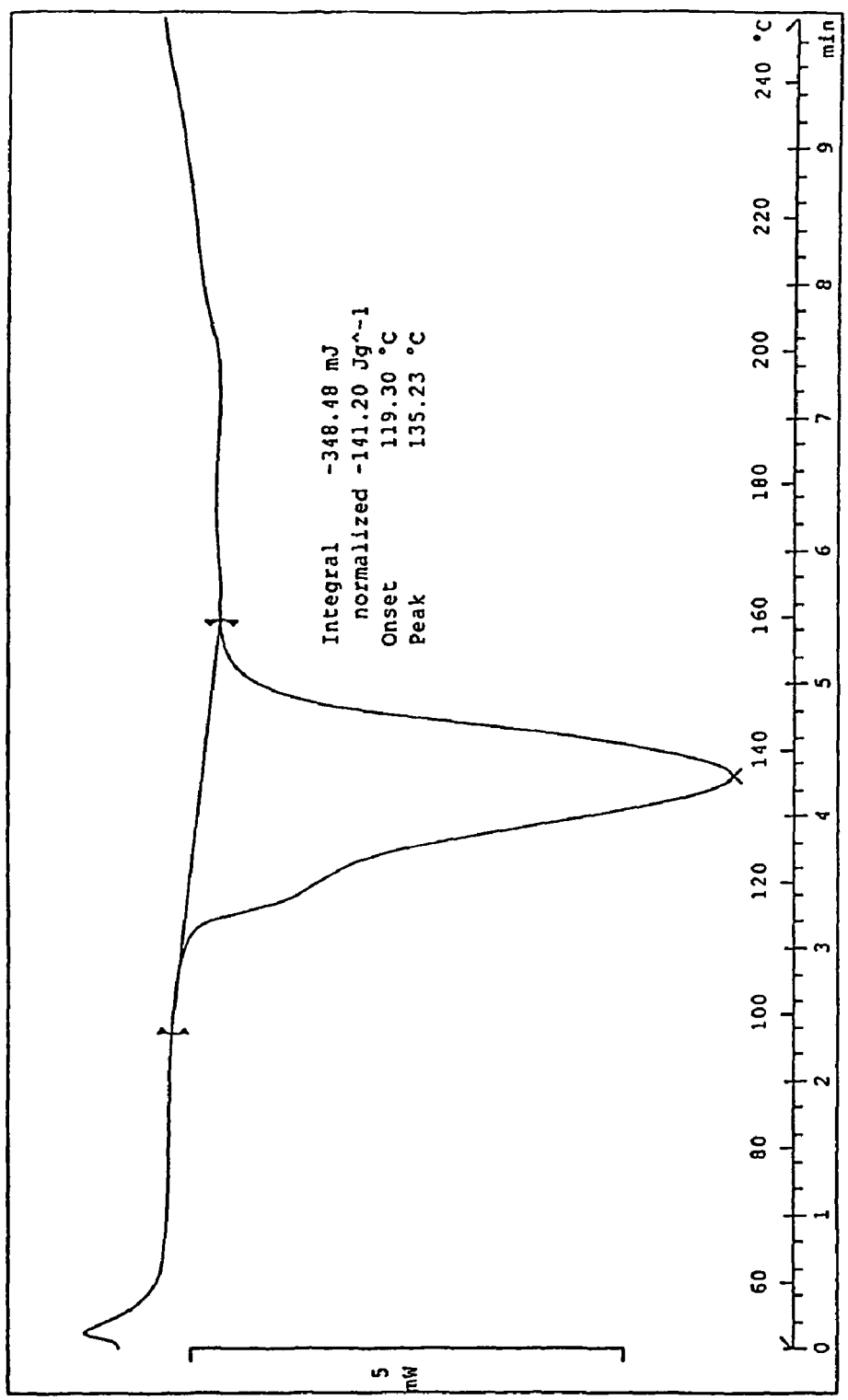
FIG. 3 shows a DSC for raloxifene L-lactate hemihydrate. The chart was recorded at a rate of 20° C./min.

The product was analysed using differential scanning calorimetry using a METTLER TOLEDO STAR® system, according to the instructions of the manufacturer. The differential scanning calorimetric chart (DSC) is shown in FIG. 3.

Figure 4:
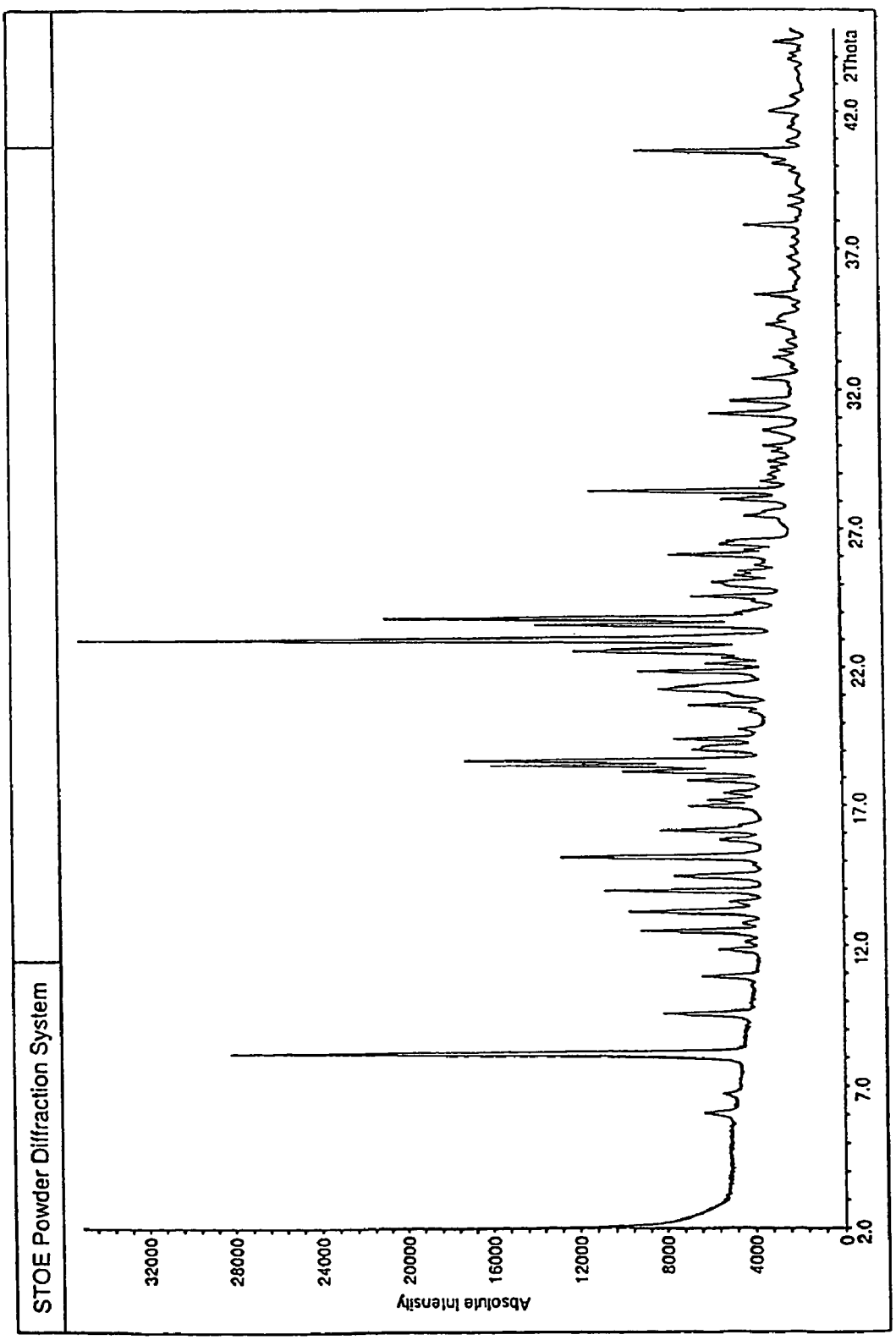
FIG. 4 shows the X-ray diffraction pattern for crystalline raloxifene L-lactate hemihydrate.

Further the product was analysed by X-ray diffraction analysis using the STOE Powder diffraction system. The result is shown in FIG. 4, and is also listed numerically below.
XRD:

| D | 2Theta | I(rel) | I(abs) | FWHM |
|---|---|---|---|---|
| 14.639874 | 6.0322 | 17.56 | 6122 | 0.1200 |
| 13.207421 | 6.6871 | 15.07 | 5254 | 0.1200 |
| 10.875932 | 8.1229 | 80.41 | 28029 | 0.1200 |
| 9.268456 | 9.5347 | 22.67 | 7903 | 0.1200 |
| 8.140638 | 10.8593 | 17.92 | 6247 | 0.1200 |
| 7.488503 | 11.8083 | 15.59 | 5433 | 0.1000 |
| 7.310331 | 12.0971 | 12.47 | 4347 | 0.0800 |
| 7.089508 | 12.4754 | 25.79 | 8991 | 0.1000 |
| 6.931874 | 12.7603 | 12.78 | 4454 | 0.0900 |
| 6.723932 | 13.1566 | 27.83 | 9701 | 0.1300 |
| 6.551458 | 13.5045 | 14.20 | 4949 | 0.0900 |
| 6.359432 | 13.9143 | 30.57 | 10656 | 0.1100 |
| 6.130010 | 14.4378 | 21.33 | 7435 | 0.1300 |
| 5.853018 | 15.1249 | 36.40 | 12687 | 0.1100 |
| 5.626204 | 15.7385 | 15.49 | 5401 | 0.1300 |
| 5.507643 | 16.0795 | 23.25 | 8106 | 0.1000 |
| 5.447238 | 16.2590 | 13.21 | 4606 | 0.0870 |
| 5.224449 | 16.9573 | 19.21 | 6697 | 0.1100 |
| 5.160516 | 17.1690 | 17.10 | 5961 | 0.0870 |
| 5.083475 | 17.4312 | 14.74 | 5137 | 0.1100 |
| 4.954247 | 17.8896 | 19.64 | 6848 | 0.1000 |
| 4.863750 | 18.2252 | 28.34 | 9879 | 0.0800 |
| 4.805168 | 18.4494 | 46.26 | 16125 | 0.0700 |
| 4.756883 | 18.6383 | 49.99 | 17425 | 0.0800 |
| 4.656926 | 19.0420 | 19.10 | 6659 | 0.1900 |
| 4.630194 | 19.1530 | 17.96 | 6260 | 0.0870 |
| 4.566015 | 19.4248 | 21.34 | 7438 | 0.1000 |
| 4.487514 | 19.7680 | 12.76 | 4447 | 0.1000 |
| 4.347753 | 20.4101 | 11.69 | 4074 | 0.1100 |
| 4.301465 | 20.6322 | 19.17 | 6682 | 0.0900 |
| 4.224555 | 21.0120 | 14.55 | 5072 | 0.0870 |
| 4.186561 | 21.2049 | 23.33 | 8134 | 0.1700 |
| 4.065767 | 21.8425 | 26.06 | 9084 | 0.1000 |
| 4.015560 | 22.1190 | 17.10 | 5929 | 0.1000 |
| 3.976949 | 22.3365 | 14.98 | 5223 | 0.0500 |
| 3.935785 | 22.5732 | 34.50 | 12028 | 0.1100 |
| 3.867038 | 22.9799 | 100.00 | 34859 | 0.1000 |
| 3.779481 | 23.5198 | 40.14 | 13991 | 0.0800 |
| 3.742319 | 23.7567 | 59.68 | 20805 | 0.1000 |
| 3.710418 | 23.9640 | 13.17 | 4591 | 0.0870 |
| 3.645564 | 24.3968 | 11.19 | 3902 | 0.0800 |
| 3.621808 | 24.5593 | 18.71 | 6524 | 0.1000 |
| 3.552536 | 25.0459 | 16.01 | 5581 | 0.1000 |
| 3.516088 | 25.3098 | 13.46 | 4691 | 0.0600 |
| 3.498357 | 25.4402 | 12.66 | 4413 | 0.0700 |
| 3.467075 | 25.6737 | 10.74 | 3745 | 0.0500 |
| 3.418947 | 26.0414 | 21.49 | 7491 | 0.1000 |
| 3.395298 | 26.2260 | 12.12 | 4225 | 0.0870 |
| 3.369948 | 26.4268 | 15.48 | 5369 | 0.0700 |
| 3.358554 | 26.5181 | 14.33 | 4995 | 0.0600 |
| 3.244985 | 27.4641 | 11.90 | 4149 | 0.0700 |
| 3.229427 | 27.5990 | 9.63 | 3356 | 0.0870 |
| 3.177657 | 28.0578 | 15.07 | 5253 | 0.1200 |
| 3.144884 | 28.3562 | 32.65 | 11381 | 0.1000 |
| 3.106130 | 28.7176 | 9.83 | 3425 | 0.0800 |
| 3.082970 | 28.9380 | 9.00 | 3138 | 0.0870 |
| 3.056106 | 29.1980 | 8.56 | 2984 | 0.0870 |
| 3.032184 | 29.4335 | 8.74 | 3048 | 0.1100 |
| 2.994539 | 29.8121 | 8.27 | 2884 | 0.0700 |
| 2.979114 | 29.9700 | 9.26 | 3229 | 0.0800 |
| 2.924922 | 30.5387 | 9.19 | 3203 | 0.1800 |
| 2.870290 | 31.1346 | 16.32 | 5689 | 0.1400 |
| 2.828902 | 31.6019 | 13.59 | 4737 | 0.1100 |
| 2.762611 | 32.3808 | 10.83 | 3775 | 0.1000 |

Example 6

[6-hydroxy-2-(4-hydroxyphenyl)benzo[b]thien-3-yl][4-[2-(1-piperidinyl)ethoxy]phenyl; Raloxifene L-lactate 37.9 g (~0.6 mol) pulverized potassium hydroxide (>85%) is dissolved in 1250 ml 2-propanol, with stirring and addition of nitrogen, over approximately 30 minutes. 100 g (0.196 mol) raloxifene hydrochloride is added in small portions in such a way that temperature is kept below 30° C. After addition of raloxifene hydrochloride, the deep red suspension is stirred for 30-45 minutes until a deep red solution appears. Reminiscence of insoluble product may be filtered off A solution of 67.6 g 85% L-lactic acid (0.6 mol) is added with violent stirring during 1-1.5 hours. The mixture is now stirred further at room temperature for 18 hours. If no or very little precipitate appears in the solution the reaction mixture is filtered and 2-propanol is evaporated off. To the reminisce is now added 150 ml of water with stirring and the precipitated product is collected by filtration and dried in vacuo at 55-65° C. Next the crude product is recrystallized from 160 ml 96% ethanol (if necessary seeding crystals are added) to give 62.8 g (56.4%) of the product.

Mp: 171-173° C.:
Elemental analysis $C_{31}H_{33}NO_7S$:
Calculated: C, 65.52%; H, 5.94%; N, 2.47%; S, 5.64%.
Found: C, 65.50%; H, 5.85%; N, 2.50%; S, 5.74%.
IR:
3159 $cm^{-1}$, 2935 $cm^{-1}$, 2806 $cm^{-1}$, 2672 $cm^{-1}$, 1643 $cm^{-1}$, 1598 $cm^{-1}$, 1574 $cm^{-1}$, 1547 $cm^{-1}$, 1501 $cm^{-1}$, 1466 $cm^{-1}$, 1422 $cm^{-1}$, 1347 $cm^{-1}$, 1308 $cm^{-1}$, 1269 $cm^{-1}$, 1229 $cm^{-1}$, 1171 $cm^{-1}$, 1119 $cm^{-1}$, 1067 $cm^{-1}$, 1037 $cm^{-1}$, 1006 $cm^{-1}$, 908 $cm^{-1}$, 835 $cm^{-1}$, 807 $cm^{-1}$, 665 $cm^{-1}$, 649 $cm^{-1}$, 634 $cm^{-1}$, 623 $cm^{-1}$, 513 $cm^{-1}$.

Figure 5:
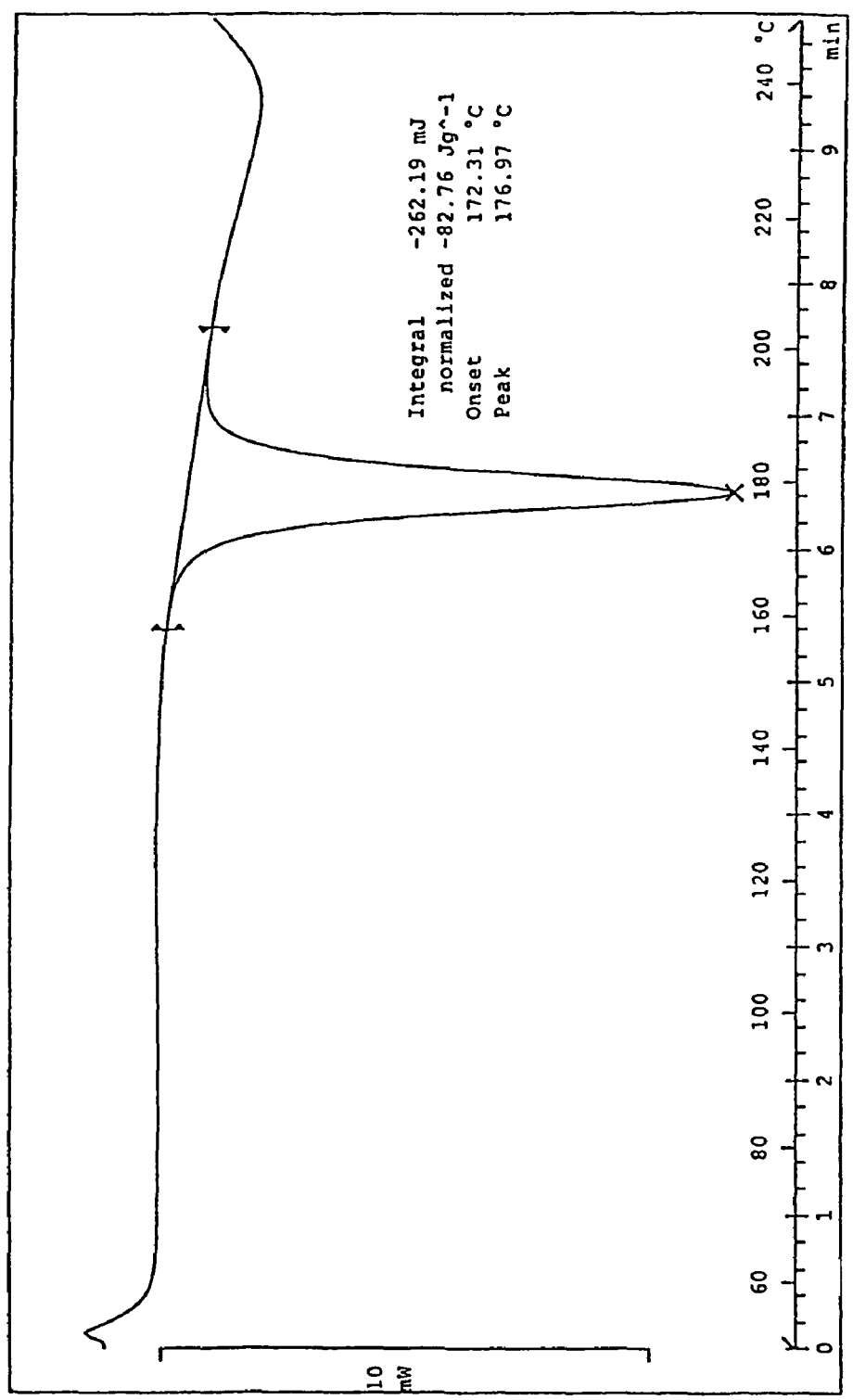
FIG. 5 shows a DSC for raloxifene L-lactate. The chart was recorded at a rate of 20° C./min.

The product was analysed using differential scanning calorimetry using a METTLER TOLEDO STAR® system, according to the instructions of the manufacturer. The differential scanning calorimetric chart (DSC) is shown in FIG. 5.

Figure 6:
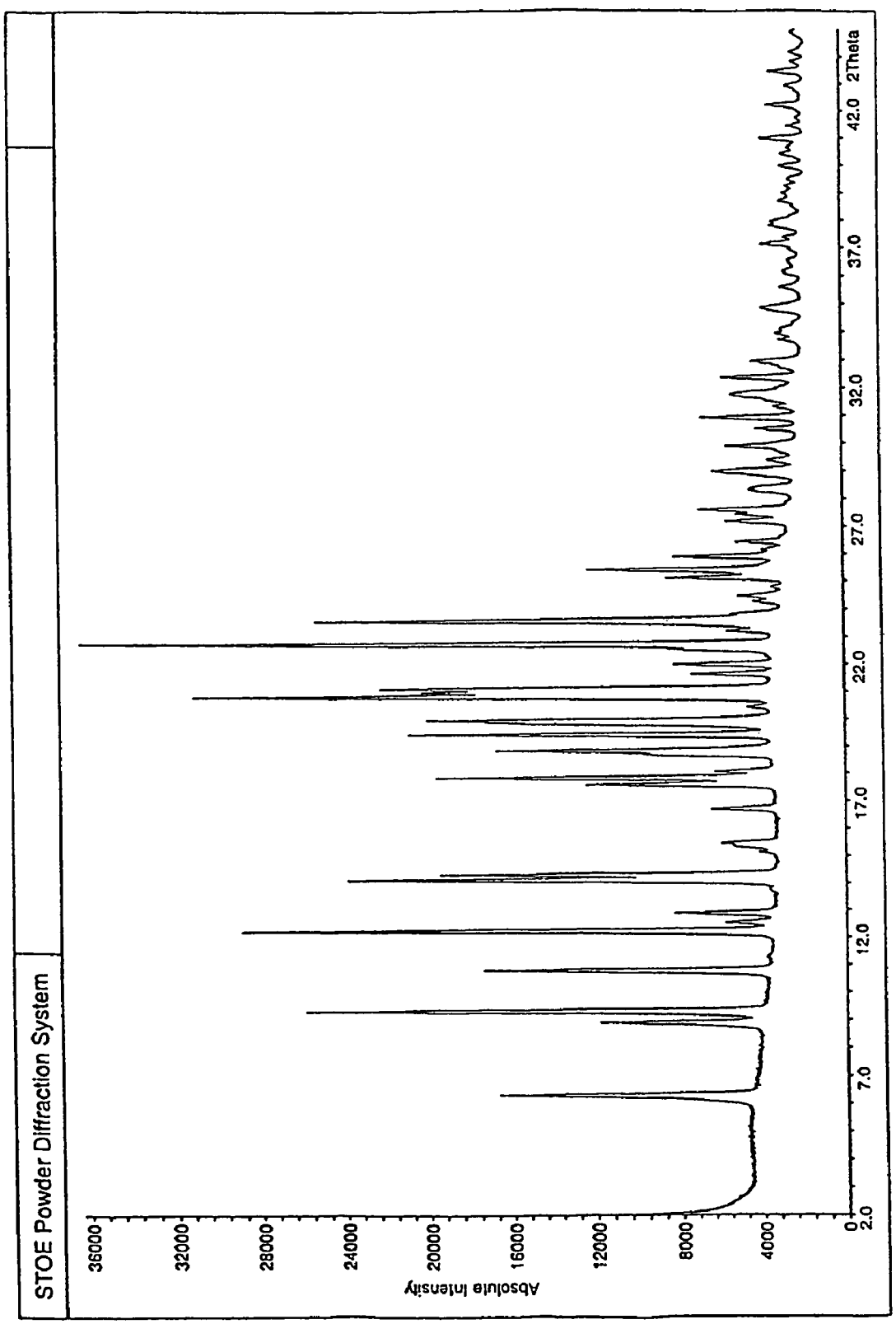
FIG. 6 shows the X-ray diffraction pattern for crystalline raloxifene L-lactate.
Figure 7:
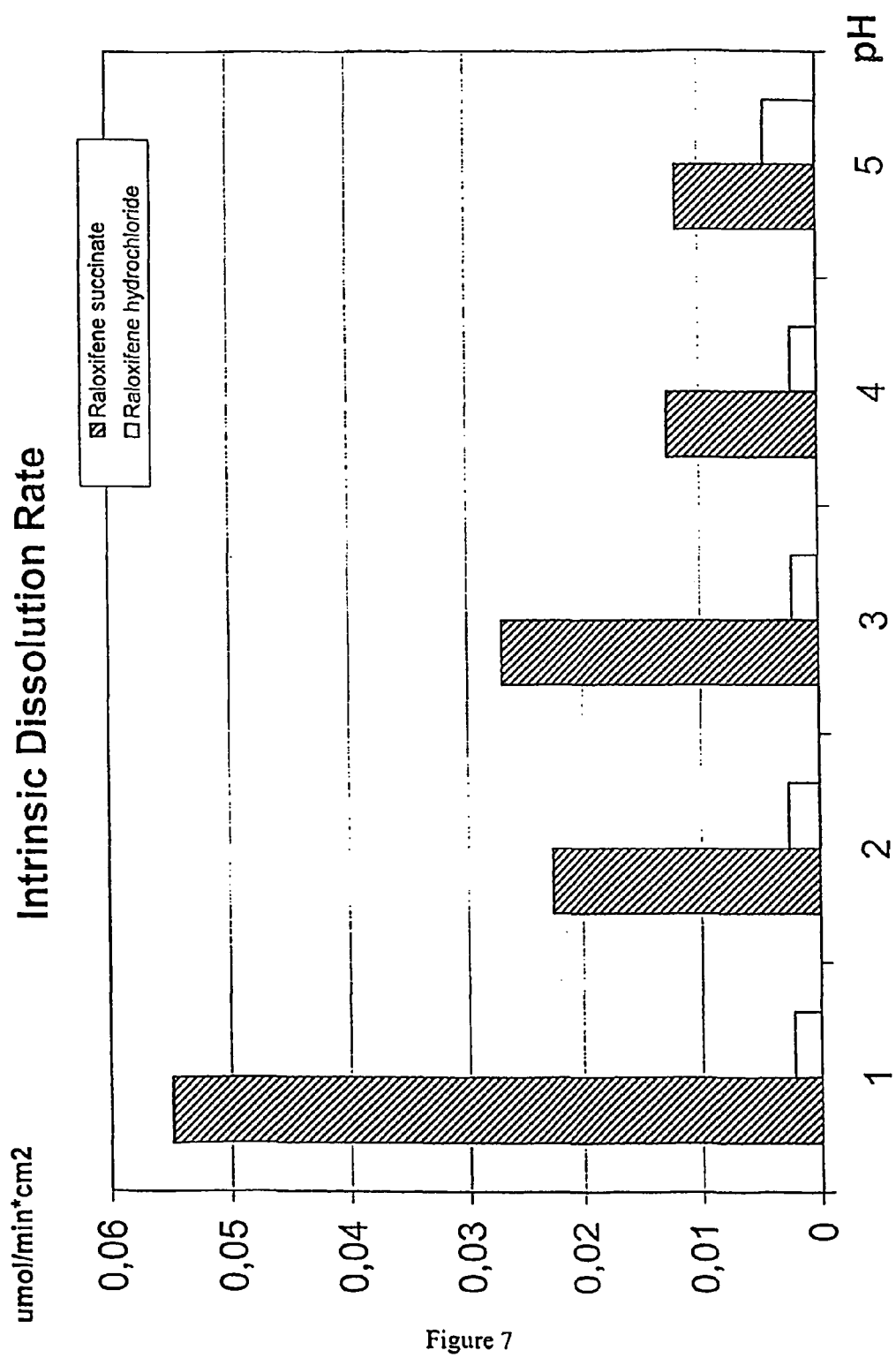
FIG. 7 shows the Intrinsic Dissolution Rate for raloxifene succinate compared with raloxifene hydrochloride.
Figure 8:
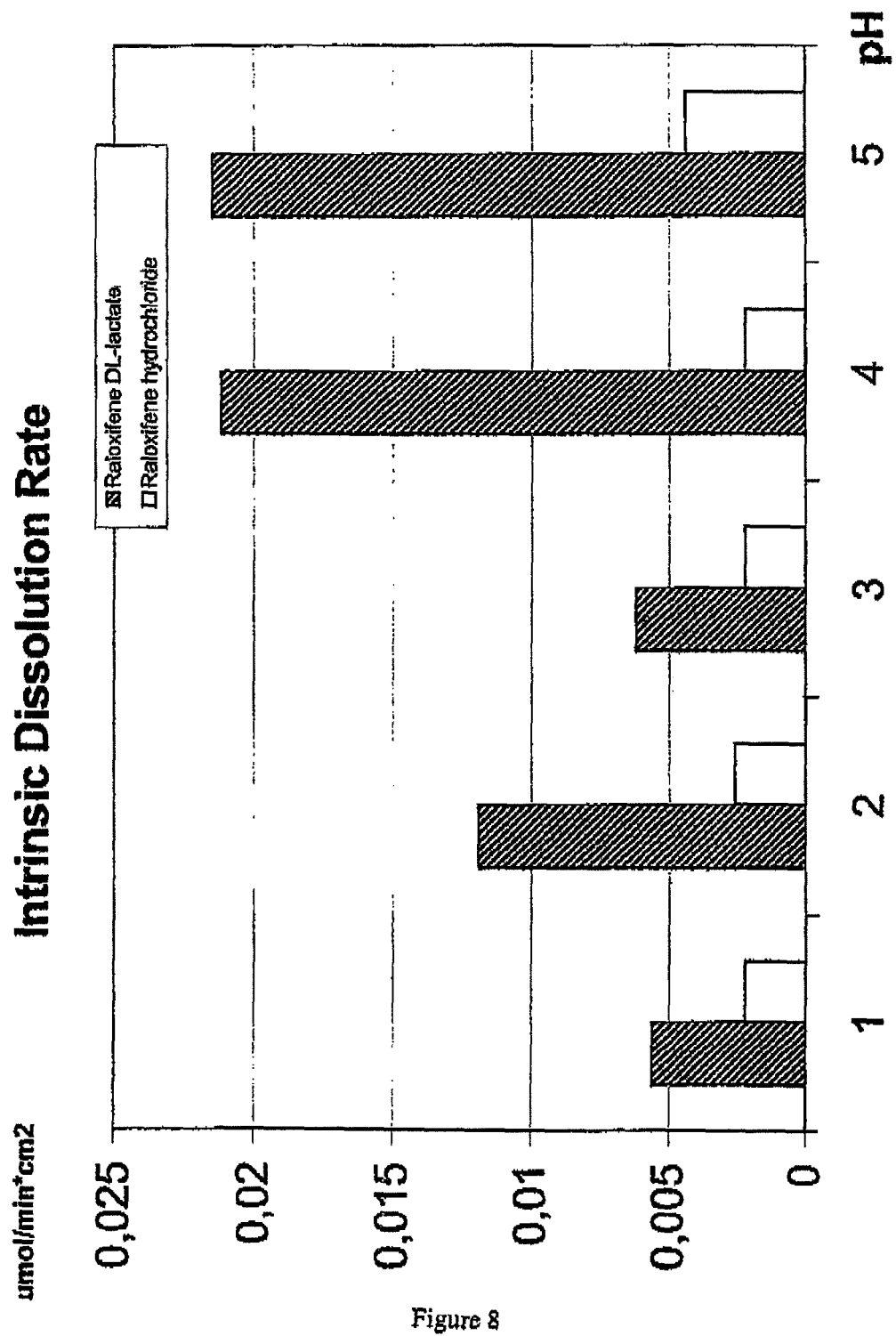
FIG. 8 shows the Intrinsic Dissolution Rate for raloxifene DL-lactate compared with raloxifene hydrochloride.
Figure 9:
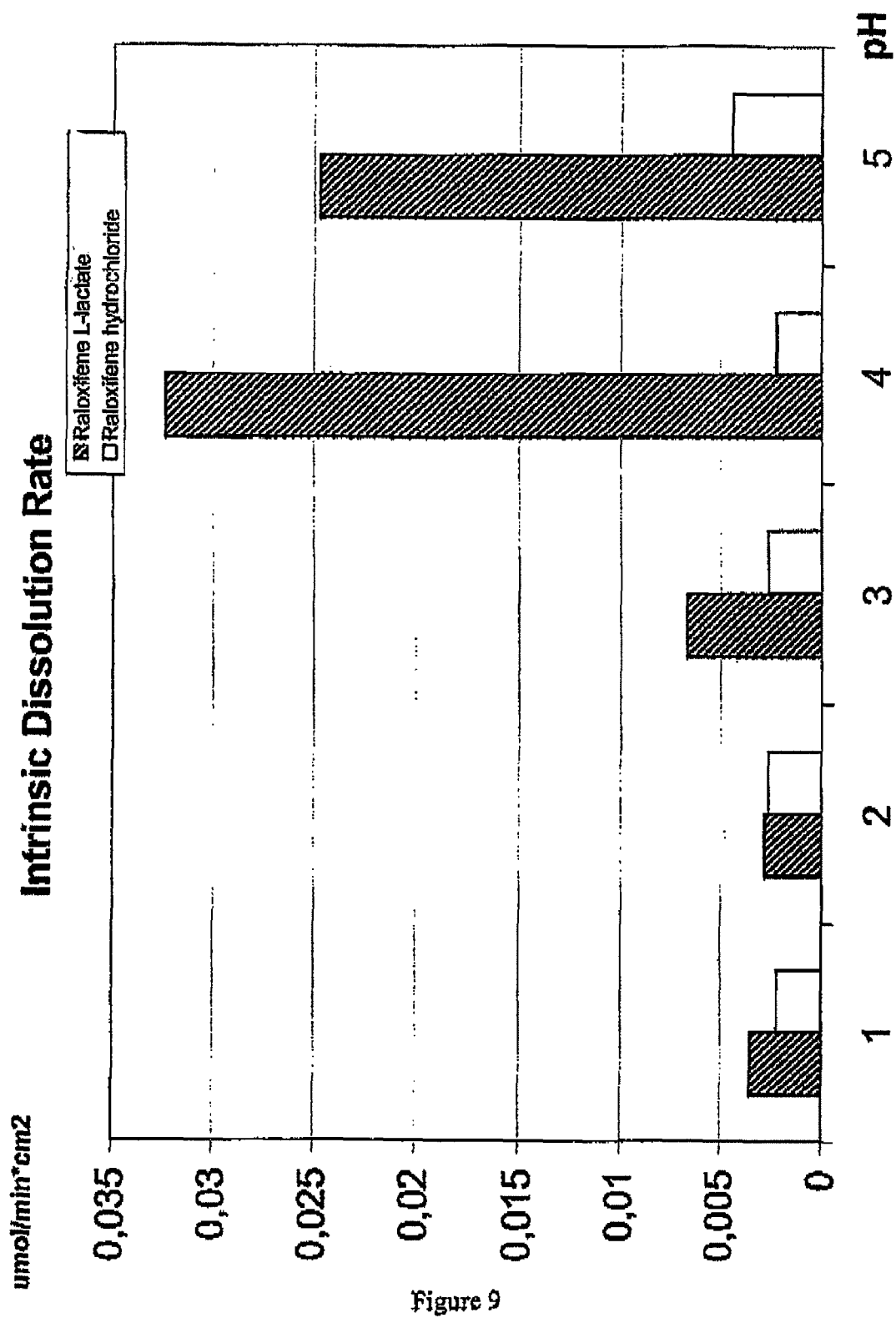
FIG. 9 shows the Intrinsic Dissolution Rate for raloxifene L-lactate compared with raloxifene hydrochloride.
Figure 10:
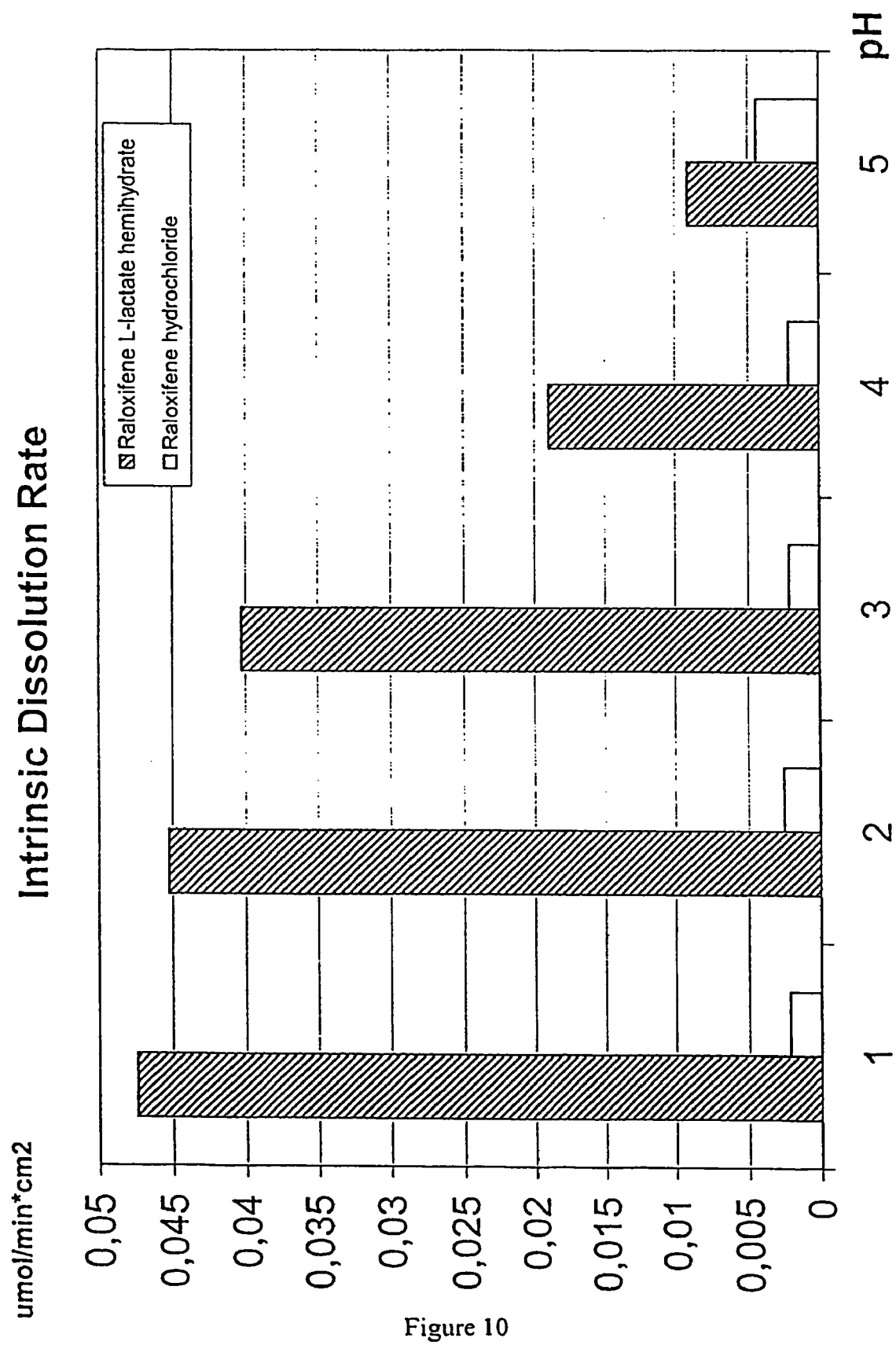
FIG. 10 shows the Intrinsic Dissolution Rate for raloxifene L-lactate hemihydrate compared with raloxifene hydrochloride.
Figure 11:
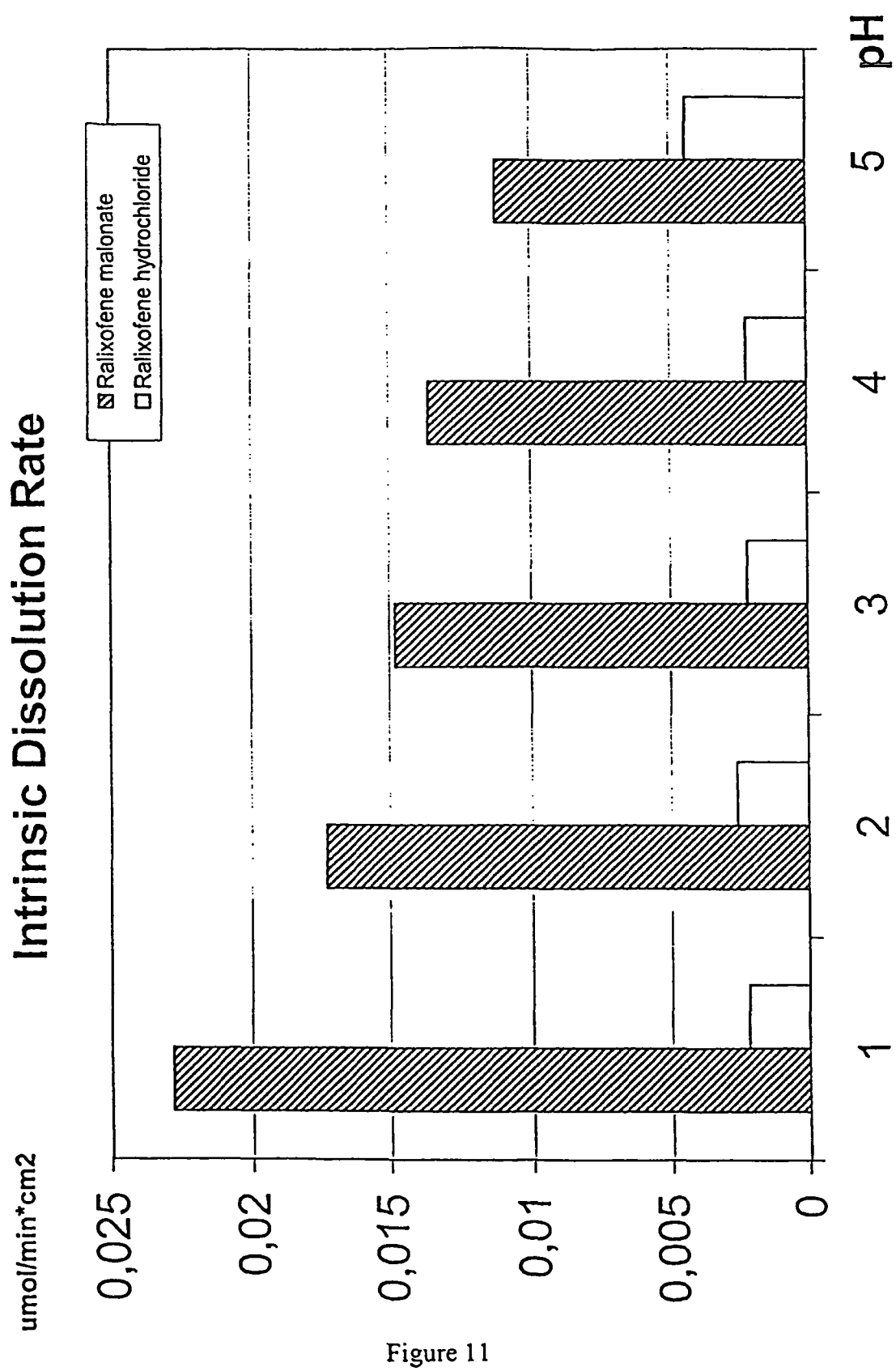
FIG. 11 shows the Intrinsic Dissolution Rate for raloxifene malonate compared with raloxifene hydrochloride.
Figure 12:
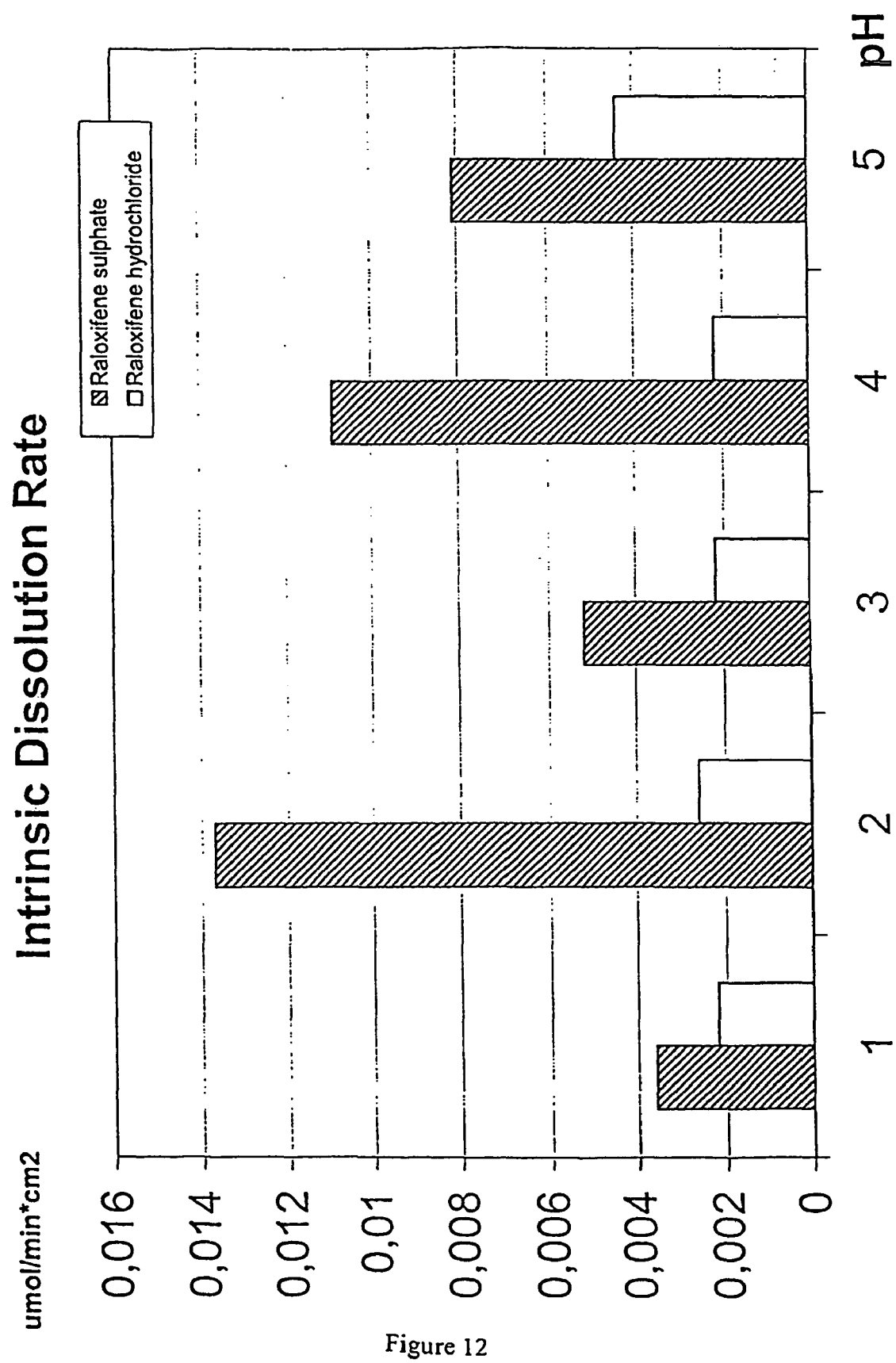
FIG. 12 shows the Intrinsic Dissolution Rate for raloxifene sulphate compared with raloxifene hydrochloride.

Further the product was analysed by X-ray diffraction analysis using the STOE Powder diffraction system. The result is shown in FIG. 6, and is also listed numerically below.
XRD:

| D | 2Theta | I(rel) | I(abs) | FWHM |
|---|---|---|---|---|
| 14.079244 | 6.2726 | 45.93 | 16568 | 0.1300 |
| 9.974912 | 8.8580 | 32.43 | 11699 | 0.1100 |
| 9.526523 | 9.2758 | 71.31 | 25721 | 0.1200 |
| 8.215598 | 10.7600 | 47.82 | 17248 | 0.1100 |
| 7.246270 | 12.2045 | 80.04 | 28871 | 0.1100 |
| 7.065557 | 12.5178 | 16.17 | 5832 | 0.0700 |
| 6.878001 | 12.8606 | 22.74 | 8201 | 0.1200 |

-continued

| D | 2Theta | I(rel) | I(abs) | FWHM |
|---|---|---|---|---|
| 6.283709 | 14.0828 | 66.27 | 23901 | 0.0800 |
| 6.194698 | 14.2862 | 53.98 | 19470 | 0.0984 |
| 5.859529 | 15.1080 | 11.17 | 4028 | 0.0984 |
| 5.744935 | 15.4112 | 16.16 | 5828 | 0.1200 |
| 5.312222 | 16.6751 | 18.02 | 6499 | 0.1200 |
| 5.046910 | 17.5585 | 34.26 | 12356 | 0.0900 |
| 4.978933 | 17.8001 | 54.66 | 19715 | 0.1000 |
| 4.918535 | 18.0205 | 17.40 | 6277 | 0.0984 |
| 4.746264 | 18.6804 | 26.77 | 9655 | 0.1000 |
| 4.712771 | 18.8143 | 46.35 | 16716 | 0.0900 |
| 4.569429 | 19.4101 | 57.60 | 20777 | 0.1000 |
| 4.455985 | 19.9093 | 53.60 | 19332 | 0.1200 |
| 4.345589 | 20.4204 | 12.70 | 4579 | 0.0900 |
| 4.268096 | 20.7952 | 86.33 | 31139 | 0.0900 |
| 4.106332 | 21.6241 | 20.17 | 7274 | 0.1100 |
| 4.042283 | 21.9710 | 22.73 | 8197 | 0.1200 |
| 3.944656 | 22.5218 | 23.46 | 8462 | 0.1000 |
| 3.913129 | 22.7056 | 100.00 | 36069 | 0.1100 |
| 3.831706 | 23.1947 | 15.49 | 5586 | 0.0900 |
| 3.777075 | 23.5350 | 69.72 | 25148 | 0.1400 |
| 3.735872 | 23.7983 | 14.85 | 5358 | 0.0984 |
| 3.667856 | 24.2463 | 11.94 | 4305 | 0.0900 |
| 3.639035 | 24.4413 | 13.87 | 5001 | 0.0800 |
| 3.589918 | 24.7809 | 9.38 | 3383 | 0.0984 |
| 3.545715 | 25.0949 | 23.58 | 8505 | 0.0800 |
| 3.505655 | 25.3864 | 33.63 | 12131 | 0.1100 |
| 3.442223 | 25.8622 | 22.60 | 8152 | 0.1100 |
| 3.411017 | 26.1030 | 10.82 | 3901 | 0.0984 |
| 3.371851 | 26.4117 | 44.16 | 5108 | 0.1000 |
| 3.280618 | 27.1600 | 15.23 | 5494 | 0.1100 |
| 3.251104 | 27.4114 | 14.23 | 5134 | 0.0800 |
| 3.232072 | 27.5760 | 19.25 | 6943 | 0.1100 |
| 3.153056 | 28.2812 | 12.42 | 4479 | 0.1900 |
| 3.143130 | 28.3724 | 12.29 | 4432 | 0.0984 |
| 3.081939 | 28.9479 | 17.16 | 6189 | 0.2200 |
| 3.040378 | 29.3524 | 9.73 | 3510 | 0.1300 |
| 2.990508 | 29.8532 | 15.29 | 5514 | 0.1400 |
| 2.929711 | 30.4876 | 11.37 | 4102 | 0.1200 |
| 2.892397 | 30.8906 | 18.91 | 6822 | 0.1200 |
| 2.856192 | 31.2922 | 8.91 | 3214 | 0.1100 |
| 2.818108 | 31.7261 | 14.79 | 5336 | 0.2500 |
| 2.765584 | 32.3450 | 15.86 | 5720 | 0.1300 |

Example 7

Preparation of [6-hydroxy-2-(4-hydroxyphenyl)benzo[b]thien-3-yl][4-[2-(1-piperidinyl)ethoxy]phenyl-, L-lactate; Raloxifene L-lactate 40 g (0.06 mol) 6-methyl sulphonyloxy-2-(4-methylsulphonyl-oxyphenyl)benzo[b]thien-3-yl][4-[2-(1-piperidinyl)ethoxy]phenyl-, hydrochlorid, having the structural formula below

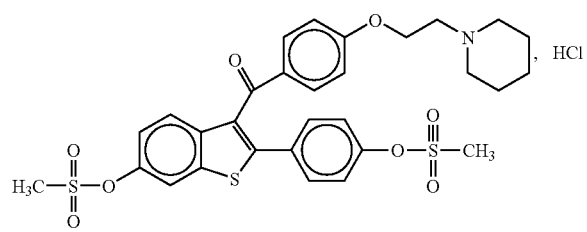

is suspended in 385 ml 2-propanol. 21.75 g (0.33 mol) powdered 85% potassium hydroxide is added with stirring, and the mixture is heated to reflux for 2 hour. The deep red solution is cooled to room temperature, and a solution of 20.3 g 85% L-lactic acid (0.18 mol) is added with violent stirring during 1-1.5 hours, and thereafter the 2-propanol is evaporated off to give the crude product. The product is recrystallized from approximately 50 ml 96% ethanol to give the title compound.

Example 8

Comparative example

Dissolution of Raloxifene Hydrochloride in Dilute Hydrochloric Acid or Phosphoric Acid 60 mg raloxifene HCl was transferred to a dissolution vessel containing one liter 0.1 M HCl. The mixture was vigorously mixed and left at room temperature over night. Subsequently the dissolution was evaluated visually. Very little of the initial added amount of raloxifene hydrochloride was dissolved shown by the presence of solid material at the bottom of the vessel and essentially no colouring of the fluid.

A similar dissolution test was performed using 60 mg raloxifene hydrochloride in 0.1 M phosphoric acid. In this case all raloxifene hydrochloride seemed to be dissolved indicated by the absence of solids on the bottom of the vessel and a strong yellow colouring of the fluid in the vessel.

Example 9

Dissolution of Raloxifene Acid Addition Salts or Solvates in Dilute Hydrochloric Acid or Phosphoric Acid Using same procedures as in example 8, raloxifene succinate, raloxifene DL-lactate, raloxifene L-lactate hemihydrate, raloxifene malonate and raloxifene sulphate (2-propanol solvate) were tested for dissolution in dilute hydrochloric acid or phosphorous acid.

All these tests showed complete dissolution shown be absence of solids in the vessel and strong colouring of the liquid.

Example 10

Intrinsic Dissolution Rate of Raloxifene Acid Addition Salts in Dilute Phosphoric Acid Compared with Dilute Hydrochloric Acid Experimental set-up:

The intrinsic dissolution rate of raloxifene succinate, raloxifene DL-lactate, raloxifene L-lactate, raloxifene L-lactate hemihydrate, raloxifene malonate, raloxifene sulphate (2-propanol solvate) and raloxifene hydrochloride were tested in dilute solutions of hydrochloric acid and in dilute solutions of phosphorous acid containing NaCl in amounts so the chloride ion concentration in each solution was 0.1 M. The tests were performed at 37° C. and at pH of 1, 2, 3, 4, and 5, respectively. The raloxifene hydrochloride salt used in these experiments was purchased from Otto Bradt GmbH (batch MA/RF/12003) while the rest of the raloxifene acid additions salts were prepared according to Example 1-6.

The experiments were carried out following the procedure of Rotation Disc Method (USP 1087) using Vankel VK 7000 Intrinsic dissolution apparatus (Vankel Technology group, W. Vankelion) equipped with Vankel 12-4120 intrinsic disc having a surface area of 0.5 cm$^2$, Vankel 12-4130 surface plate, Vankel 12-4140 punch, and Vankel shaft and holder (surface area: 0.5 cm$^2$) and operating at a rotation rate of 100 rpm.

The buffer solution is handled in a 750 ml measuring bottle, degassed and transferred into a dissolution vessel. Approximately 100 mg compound is weighed out and transferred into an intrinsic disc. Said disc is then assembled, and to said disc a disc is applied in the IR-press at a pressure of 5 kN for 1 minute. The disc is started and samples of 10 ml are collected by use of "pressure vials" after 1, 10, 20, 30, 45, and 60 minutes. The change of volume is corrected using the equation:

$$Q = Vs \times (sumCn-1) + Cn \times Vt$$

wherein Q designates the volume at the time t, C designates the concentration of the sample n, Vt designates the volume of the liquid collected at the time t, and Vs designates the volume of the sample collected. The sample is measured against a standard using HPLC. In these measurements a 5 microns 3.9×150 mm column filled with symmetrical material is employed and as eluant a 20 mM phosphate buffer $KH_2PO_4$, pH 6.8 mixed with acetonitrile and tetrahydrofuran in the ratio 55:35:10 is used.

Preparation of Standard Solution:

The standard is prepared by use of following procedure: 20 mg of salt is dissolved initially in 100 ml of MeOH and then 1 ml of this solution is transferred to a 50 ml flask with water and then 2 ml to a 20 ml flask of buffer in question.

Preparation of Buffer Solutions:

pH 1: a 0.1 M HCl is used.

0.025 M Phosphate buffer solution pH 2.0: 3.40 g of potassium dihydrogen phosphate is dissolved in 900 ml of water. Then pH is adjusted to 2.0 with phosphoric acid and diluted to 1000.0 ml with water. Exactly 5.85 g of NaCl is added to 1 L of buffer.

0.025 M Phosphate buffer solution pH 3.0: 3.40 g of potassium dihydrogen phosphate is dissolved in 900 ml of water. Then pH is adjusted to 3.0 with phosphoric acid and diluted to 1000.0 ml with water. Exactly 5.85 g of NaCl is added to 1 L of buffer.

0.022 M Phosphate buffer solution pH 4.0: 3.0 g of potassium dihydrogen phosphate is dissolved in 800 ml of water. Then pH is adjusted with 1 M potassium hydroxide and phosphoric acid and diluted to 1000.0 ml with water. Exactly 5.85 g of NaCl is added to 1 L of buffer. 0.02 M Phosphate buffer solution pH 5.0: 2.72 g of potassium dihydrogen phosphate is dissolved in 800 ml of water. Then pH is adjusted with 1 M potassium hydroxide and diluted to 1000.0 ml with water. Exactly 5.85 g of NaCl is added to 1 L of buffer.

Results

The results from above described experiment comparing the ID of the various raloxifene acid addition salts in dilute solutions of phosphorous acid and hydrochloric acid, respectively, is given in the table below. The numbers in the table represent the average of two measurements.

| Buffer solution | Succinate | DL-lactate hemi-hydrate | L-Lactate ¼-hydrate | L-lactate hemi-hydrate | Malonate | Sulphate | Hydrochloride |
|---|---|---|---|---|---|---|---|
| Hydrochloride, pH 1 | 0.0550 | 0.0056 | 0.0035 | 0.0475 | 0.0229 | 0.0036 | 0.0022 |
| Phosphate, pH 2 | 0.0228 | 0.0119 | 0.0028 | 0.0453 | 0.0173 | 0.0137 | 0.0026 |
| Phosphate, pH 3 | 0.0271 | 0.0062 | 0.0067 | 0.0403 | 0.0148 | 0.0052 | 0.0022 |
| Phosphate, pH 4 | 0.0127 | 0.0212 | 0.0324 | 0.0190 | 0.0136 | 0.0109 | 0.0022 |
| Phosphate, pH 5 | 0.0119 | 0.0215 | 0.0247 | 0.0091 | 0.0112 | 0.0081 | 0.0044 |

The intrinsic dissolution rate (IDR) in (µmol/min * $cm^2$) of various acid addition salts of raloxifene determined by the method described above.
The numbers represent the average of two measurements.

Graphic displays of the results are shown in the FIGS. 7-12. The results show very clearly that the intrinsic dissolution rate is markedly higher for the raloxifene acid addition salts and/or solvates thereof according to the invention compared with raloxifene hydrochloride.

The invention claimed is:

1. Raloxifene DL-lactate anhydrate being in crystalline form having the following X-ray crystalline positions:
XRD:

| D | 2Theta | I(rel) | I(abs) | FWHM |
|---|---|---|---|---|
| 13.595814 | 6.4959 | 28.40 | 12683 | 0.1400 |
| 10.855533 | 8.1382 | 16.15 | 7211 | 0.1200 |
| 9.849394 | 8.9711 | 32.17 | 14369 | 0.1000 |
| 9.534325 | 9.2682 | 66.95 | 29898 | 0.1300 |
| 8.150249 | 10.8465 | 45.20 | 20188 | 0.1300 |
| 7.240730 | 12.2138 | 63.53 | 28374 | 0.1400 |
| 6.769843 | 13.0670 | 18.42 | 8227 | 0.1500 |
| 6.272666 | 14.1077 | 75.67 | 33794 | 0.1900 |
| 5.818832 | 15.2143 | 13.28 | 5933 | 0.2000 |
| 5.657337 | 15.6513 | 18.07 | 8070 | 0.1300 |
| 5.505030 | 16.0872 | 10.51 | 4692 | 0.1000 |
| 5.261933 | 16.8357 | 17.48 | 7806 | 0.1400 |
| 5.089504 | 17.4104 | 16.14 | 7210 | 0.1000 |
| 5.001569 | 17.7189 | 41.94 | 18732 | 0.0900 |
| 4.958950 | 17.8725 | 29.16 | 13023 | 0.1148 |
| 4.797388 | 18.4795 | 19.39 | 8660 | 0.1100 |
| 4.669322 | 18.9910 | 49.20 | 21972 | 0.1400 |
| 4.574684 | 19.3876 | 63.21 | 28227 | 0.1000 |
| 4.533019 | 19.5676 | 44.94 | 20071 | 0.1148 |
| 4.440548 | 19.9792 | 32.70 | 14604 | 0.1200 |
| 4.301886 | 20.6301 | 100.00 | 44659 | 0.1500 |
| 4.155406 | 21.3657 | 78.00 | 34833 | 0.1600 |
| 4.059049 | 21.8797 | 27.53 | 12296 | 0.1800 |
| 3.960846 | 22.4285 | 25.59 | 11427 | 0.1000 |
| 3.907408 | 22.7393 | 83.48 | 37282 | 0.1200 |
| 3.865461 | 22.9894 | 16.46 | 7350 | 0.1148 |
| 3.828892 | 23.2120 | 17.46 | 7798 | 0.0900 |
| 3.773130 | 23.5599 | 50.71 | 22649 | 0.1200 |
| 3.716486 | 23.9243 | 23.06 | 10300 | 0.1300 |
| 3.652238 | 24.3515 | 15.79 | 7053 | 0.1800 |
| 3.584725 | 24.8174 | 12.91 | 5764 | 0.1500 |
| 3.486791 | 25.5261 | 30.45 | 13600 | 0.1200 |
| 3.439149 | 25.8858 | 22.21 | 9919 | 0.1300 |
| 3.396267 | 26.2184 | 17.86 | 7978 | 0.1100 |
| 3.370045 | 26.4261 | 12.48 | 5572 | 0.1148 |
| 3.329320 | 26.7553 | 9.21 | 4113 | 0.1100 |

-continued

| D | 2Theta | I(rel) | I(abs) | FWHM |
|---|---|---|---|---|
| 3.292728 | 27.0582 | 11.81 | 5274 | 0.1000 |
| 3.278070 | 27.1815 | 11.25 | 5026 | 0.1148 |
| 3.218620 | 27.6935 | 21.24 | 9485 | 0.1900 |
| 3.167986 | 28.1452 | 13.80 | 6162 | 0.0900 |
| 3.143230 | 28.3715 | 30.33 | 13546 | 0.1000 |
| 3.095423 | 28.9191 | 14.02 | 6260 | 0.1200 |
| 3.024921 | 29.5058 | 11.56 | 5161 | 0.1400 |
| 3.007253 | 29.6831 | 13.40 | 5984 | 0.1300. |

2. Raloxifene DL-lactate anhydrate being in crystalline form having the following X-ray crystalline positions:
   XRD:

| D | 2Theta | I(rel) | I(abs) | FWHM |
|---|---|---|---|---|
| 9.534325 | 9.2682 | 66.95 | 29898 | 0.1300 |
| 8.150249 | 10.8465 | 45.20 | 20188 | 0.1300 |
| 7.240730 | 12.2138 | 63.53 | 28374 | 0.1400 |
| 6.272666 | 14.1077 | 75.67 | 33794 | 0.1900 |
| 4.669322 | 18.9910 | 49.20 | 21972 | 0.1400 |
| 4.574684 | 19.3876 | 63.21 | 28227 | 0.1000 |
| 4.301886 | 20.6301 | 100.00 | 44659 | 0.1500 |
| 4.155406 | 21.3657 | 78.00 | 34833 | 0.1600 |
| 3.907408 | 22.7393 | 83.48 | 37282 | 0.1200 |
| 3.773130 | 23.5599 | 50.71 | 22649 | 0.1200. |

3. Raloxifene DL-lactate being in crystalline form having the following X-ray crystalline positions:
   XRD:

| D | 2Theta | I(rel) | I(abs) | FWHM |
|---|---|---|---|---|
| 13.595814 | 6.4959 | 28.40 | 12683 | 0.1400 |
| 10.855533 | 8.1382 | 16.15 | 7211 | 0.1200 |
| 9.849394 | 8.9711 | 32.17 | 14369 | 0.1000 |
| 9.534325 | 9.2682 | 66.95 | 29898 | 0.1300 |
| 8.150249 | 10.8465 | 45.20 | 20188 | 0.1300 |
| 7.240730 | 12.2138 | 63.53 | 28374 | 0.1400 |
| 6.769843 | 13.0670 | 18.42 | 8227 | 0.1500 |
| 6.272666 | 14.1077 | 75.67 | 33794 | 0.1900 |
| 5.818832 | 15.2143 | 13.28 | 5933 | 0.2000 |
| 5.657337 | 15.6513 | 18.07 | 8070 | 0.1300 |
| 5.505030 | 16.0872 | 10.51 | 4692 | 0.1000 |
| 5.261933 | 16.8357 | 17.48 | 7806 | 0.1400 |
| 5.089504 | 17.4104 | 16.14 | 7210 | 0.1000 |
| 5.001569 | 17.7189 | 41.94 | 18732 | 0.0900 |

-continued

| D | 2Theta | I(rel) | I(abs) | FWHM |
|---|---|---|---|---|
| 4.958950 | 17.8725 | 29.16 | 13023 | 0.1148 |
| 4.797388 | 18.4795 | 19.39 | 8660 | 0.1100 |
| 4.669322 | 18.9910 | 49.20 | 21972 | 0.1400 |
| 4.574684 | 19.3876 | 63.21 | 28227 | 0.1000 |
| 4.533019 | 19.5676 | 44.94 | 20071 | 0.1148 |
| 4.440548 | 19.9792 | 32.70 | 14604 | 0.1200 |
| 4.301886 | 20.6301 | 100.00 | 44659 | 0.1500 |
| 4.155406 | 21.3657 | 78.00 | 34833 | 0.1600 |
| 4.059049 | 21.8797 | 27.53 | 12296 | 0.1800 |
| 3.960846 | 22.4285 | 25.59 | 11427 | 0.1000 |
| 3.907408 | 22.7393 | 83.48 | 37282 | 0.1200 |
| 3.865461 | 22.9894 | 16.46 | 7350 | 0.1148 |
| 3.828892 | 23.2120 | 17.46 | 7798 | 0.0900 |
| 3.773130 | 23.5599 | 50.71 | 22649 | 0.1200 |
| 3.716486 | 23.9243 | 23.06 | 10300 | 0.1300 |
| 3.652238 | 24.3515 | 15.79 | 7053 | 0.1800 |
| 3.584725 | 24.8174 | 12.91 | 5764 | 0.1500 |
| 3.486791 | 25.5261 | 30.45 | 13600 | 0.1200 |
| 3.439149 | 25.8858 | 22.21 | 9919 | 0.1300 |
| 3.396267 | 26.2184 | 17.86 | 7978 | 0.1100 |
| 3.370045 | 26.4261 | 12.48 | 5572 | 0.1148 |
| 3.329320 | 26.7553 | 9.21 | 4113 | 0.1100 |
| 3.292728 | 27.0582 | 11.81 | 5274 | 0.1000 |
| 3.278070 | 27.1815 | 11.25 | 5026 | 0.1148 |
| 3.218620 | 27.6935 | 21.24 | 9485 | 0.1900 |
| 3.167986 | 28.1452 | 13.80 | 6162 | 0.0900 |
| 3.143230 | 28.3715 | 30.33 | 13546 | 0.1000 |
| 3.095423 | 28.9191 | 14.02 | 6260 | 0.1200 |
| 3.024921 | 29.5058 | 11.56 | 5161 | 0.1400 |
| 3.007253 | 29.6831 | 13.40 | 5984 | 0.1300. |

4. Raloxifene DL-lactate being in crystalline form having the following X-ray crystalline positions:
   XRD:

| D | 2Theta | I(rel) | I(abs) | FWHM |
|---|---|---|---|---|
| 9.534325 | 9.2682 | 66.95 | 29898 | 0.1300 |
| 8.150249 | 10.8465 | 45.20 | 20188 | 0.1300 |
| 7.240730 | 12.2138 | 63.53 | 28374 | 0.1400 |
| 6.272666 | 14.1077 | 75.67 | 33794 | 0.1900 |
| 4.669322 | 18.9910 | 49.20 | 21972 | 0.1400 |
| 4.574684 | 19.3876 | 63.21 | 28227 | 0.1000 |
| 4.301886 | 20.6301 | 100.00 | 44659 | 0.1500 |
| 4.155406 | 21.3657 | 78.00 | 34833 | 0.1600 |
| 3.907408 | 22.7393 | 83.48 | 37282 | 0.1200 |
| 3.773130 | 23.5599 | 50.71 | 22649 | 0.1200. |

\* \* \* \* \*